United States Patent
DeKorver et al.

(10) Patent No.: US 10,231,452 B2
(45) Date of Patent: Mar. 19, 2019

(54) THIOPICOLINAMIDE COMPOUNDS WITH FUNGICIDAL ACTIVITY

(71) Applicant: Dow AgroSciences LLC, Indianapolis, IN (US)

(72) Inventors: Kyle A. DeKorver, Lafayette, IN (US); Kevin G. Meyer, Zionsville, IN (US); Chenglin Yao, Westfield, IN (US); Karla Bravo-Altamirano, Carmel, IN (US); Ronald J. Heemstra, Fishers, IN (US); Brannon Sam, Zionsville, IN (US); David M. Jones, Zionsville, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 15/690,740

(22) Filed: Aug. 30, 2017

(65) Prior Publication Data

US 2018/0055052 A1 Mar. 1, 2018

Related U.S. Application Data

(60) Provisional application No. 62/381,259, filed on Aug. 30, 2016, provisional application No. 62/381,268, filed on Aug. 30, 2016, provisional application No. 62/381,273, filed on Aug. 30, 2016, provisional application No. 62/381,279, filed on Aug. 30, 2016, provisional application No. 62/381,287, filed on Aug. 30, 2016, provisional application No. 62/381,285, filed on Aug. 30, 2016, provisional application No. 62/381,280, filed on Aug. 30, 2016, provisional application No. 62/381,282, filed on Aug. 30, 2016.

(51) Int. Cl.
| | |
|---|---|
| *A01N 43/40* | (2006.01) |
| *C07D 213/83* | (2006.01) |
| *A01N 43/90* | (2006.01) |
| *C07D 213/81* | (2006.01) |
| *C07D 213/89* | (2006.01) |

(52) U.S. Cl.
CPC .............. *A01N 43/40* (2013.01); *A01N 43/90* (2013.01); *C07D 213/81* (2013.01); *C07D 213/83* (2013.01); *C07D 213/89* (2013.01)

(58) Field of Classification Search
CPC .............................. A01N 43/40; C07D 213/83
See application file for complete search history.

(56) References Cited

U.S. PATENT DOCUMENTS

| | | | |
|---|---|---|---|
| 4,051,173 A | 9/1977 | Schact et al. | |
| 5,401,871 A | 3/1995 | Feldmann-Krane et al. | |
| 6,355,660 B1 | 3/2002 | Ricks et al. | |
| 6,410,572 B1 | 6/2002 | Schelberger et al. | |
| 6,436,421 B1 | 8/2002 | Schindler et al. | |
| 6,521,622 B1 | 2/2003 | Ricks et al. | |
| 6,706,740 B2 | 3/2004 | Ricks et al. | |
| 6,861,390 B2 | 3/2005 | Meyer et al. | |
| 6,903,219 B2 | 6/2005 | Niyaz et al. | |
| 6,916,932 B2 | 7/2005 | Meyer et al. | |
| 6,927,225 B2 | 8/2005 | Ricks | |
| 7,034,035 B2 | 4/2006 | Ricks et al. | |
| 7,183,278 B1 | 2/2007 | Sakanaka | |
| 7,241,804 B1 | 7/2007 | Hockenberry et al. | |
| 7,250,389 B1 | 7/2007 | Sakanaka | |
| RE39,991 E | 1/2008 | Ricks et al. | |
| 7,442,672 B2 | 12/2008 | Muller et al. | |
| 7,459,581 B2 | 12/2008 | Derrer et al. | |
| 7,560,565 B2 | 7/2009 | Bacque et al. | |
| 7,927,617 B2 | 4/2011 | Koltzenburg | |
| 8,008,231 B2 | 8/2011 | Leatherman | |
| 8,153,819 B2 | 4/2012 | Dietz | |
| 8,236,962 B2 | 8/2012 | Hoekstra et al. | |
| 8,349,877 B2 | 1/2013 | Brix et al. | |
| 8,415,274 B2 | 4/2013 | Wachendorff-Neumann et al. | |
| 8,470,840 B2 | 6/2013 | Klittich et al. | |
| 8,476,193 B2 | 7/2013 | Keeney et al. | |
| 8,586,550 B2 | 11/2013 | Lee et al. | |
| 8,604,215 B2 | 12/2013 | Phiasivongsa et al. | |
| 8,748,431 B2 * | 6/2014 | Sulzer-Mosse | C07D 401/14 514/249 |
| 8,785,479 B2 | 7/2014 | Meyer et al. | |
| 8,835,462 B2 | 9/2014 | Meyer et al. | |
| 8,883,811 B2 | 11/2014 | Owen et al. | |
| 8,916,579 B2 | 12/2014 | Boebel | |
| 9,006,259 B2 | 4/2015 | Boebel et al. | |
| 9,084,418 B2 | 7/2015 | Ehr et al. | |
| 9,131,690 B2 * | 9/2015 | Meyer | A01N 43/40 |
| 9,144,239 B2 | 9/2015 | Meyer et al. | |
| 9,155,305 B2 | 10/2015 | Gary | |
| 9,156,816 B2 | 10/2015 | Ito et al. | |
| 9,179,674 B2 | 11/2015 | Martin et al. | |
| 9,185,911 B2 | 11/2015 | Inami et al. | |
| 9,198,419 B2 | 12/2015 | Owen et al. | |

(Continued)

FOREIGN PATENT DOCUMENTS

| | | |
|---|---|---|
| CN | 102638989 | 8/2012 |
| EP | 1054011 | 11/2000 |

(Continued)

OTHER PUBLICATIONS

Hanafi, et al., "UK-2A, B, C and D, Novel Antifungal Antibiotics from *Streptomyces* sp. 517-02 II. Structural Elucidation", The Journal of Antibiotics, vol. 49, No. 12, pp. 1226-1231 (1996).

(Continued)

*Primary Examiner* — Golam M Shameem

(57) ABSTRACT

This disclosure relates to thiopicolinamides of Formula I and their use as fungicides.

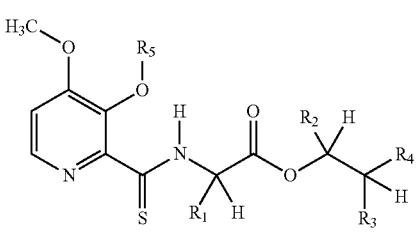

7 Claims, No Drawings

(56) References Cited

U.S. PATENT DOCUMENTS

| | | | |
|---|---|---|---|
| 9,247,741 B2 | 2/2016 | DeLorbe et al. |
| 9,265,253 B2 | 2/2016 | Li et al. |
| 9,271,496 B2 | 3/2016 | Kemmitt |
| 9,414,596 B2 | 8/2016 | Hoekstra et al. |
| 9,439,422 B2 | 9/2016 | Martin et al. |
| 9,549,555 B2 | 1/2017 | DeLorbe et al. |
| 9,549,556 B2 | 1/2017 | DeKorver et al. |
| 9,629,365 B2 | 4/2017 | Li et al. |
| 9,681,664 B2 | 6/2017 | LaLonde et al. |
| 9,686,984 B2 | 6/2017 | DeKorver et al. |
| 9,700,047 B2 | 7/2017 | Lu |
| 9,750,248 B2 | 9/2017 | Ouimette et al. |
| 2002/0119979 A1 | 8/2002 | Degenhardt et al. |
| 2002/0177578 A1 | 11/2002 | Ricks et al. |
| 2003/0018012 A1 | 1/2003 | Ricks |
| 2003/0018052 A1 | 1/2003 | Ricks |
| 2003/0022902 A1 | 1/2003 | Ricks et al. |
| 2003/0022903 A1 | 1/2003 | Ricks et al. |
| 2005/0239873 A1 | 10/2005 | Hockenberry et al. |
| 2007/0010401 A1 | 1/2007 | Noon |
| 2007/0066629 A1 | 3/2007 | Tormo i Biasco et al. |
| 2009/0203770 A1 | 8/2009 | Hockenberry et al. |
| 2009/0306142 A1 | 12/2009 | Carson et al. |
| 2010/0016163 A1 | 1/2010 | Keiper et al. |
| 2011/0070278 A1 | 3/2011 | Lopez |
| 2011/0082162 A1 | 4/2011 | Lorsbach et al. |
| 2012/0245031 A1 | 9/2012 | Gewehr et al. |
| 2013/0296372 A1 | 11/2013 | Owen et al. |
| 2014/0051678 A1 | 2/2014 | Clement-Schatlo et al. |
| 2014/0128411 A1 | 5/2014 | Ogawa et al. |
| 2014/0187587 A1 | 7/2014 | Ouimette et al. |
| 2014/0357713 A1 | 12/2014 | Damaj et al. |
| 2015/0018374 A1 | 1/2015 | Taggi et al. |
| 2015/0065529 A1 | 3/2015 | Owen et al. |
| 2015/0181868 A1 | 7/2015 | DeKorver et al. |
| 2015/0289508 A1 | 10/2015 | Meyer et al. |
| 2015/0322051 A1 | 11/2015 | Lu et al. |
| 2016/0007601 A1 | 1/2016 | Boebel et al. |
| 2016/0037774 A1 | 2/2016 | Schulz |
| 2016/0183526 A1 | 6/2016 | Hopkins et al. |
| 2016/0183527 A1 | 6/2016 | Hopkins et al. |
| 2016/0183528 A1 | 6/2016 | Hopkins et al. |
| 2017/0183324 A1 | 6/2017 | Li et al. |
| 2017/0273303 A1 | 9/2017 | DeKorver et al. |
| 2017/0273306 A1 | 9/2017 | LaLonde et al. |
| 2017/0290333 A1 | 10/2017 | Bravo-Altamirano et al. |
| 2017/0295792 A1 | 10/2017 | Bravo-Altamirano et al. |

FOREIGN PATENT DOCUMENTS

| | | |
|---|---|---|
| EP | 1516874 | 3/2005 |
| WO | WO/1996/37472 | 11/1996 |
| WO | WO/1999/40081 | 8/1999 |
| WO | WO/1999/011127 | 11/1999 |
| WO | WO/2001/014339 | 3/2001 |
| WO | WO/2001/014365 | 3/2001 |
| WO | WO/2003/011857 | 2/2003 |
| WO | WO/2003/035617 | 5/2003 |
| WO | WO/2007/017416 | 2/2007 |
| WO | WO/2009/040397 | 9/2008 |
| WO | WO/2011/028657 | 3/2011 |
| WO | WO/2011/044213 | 4/2011 |
| WO | WO/2011/069893 | 6/2011 |
| WO | WO/2012/016972 | 2/2012 |
| WO | WO/2012/016989 | 2/2012 |
| WO | WO/2012/020777 | 2/2012 |
| WO | WO/2012/070015 | 5/2012 |
| WO | WO/2013/110002 | 7/2013 |
| WO | WO/2013/116251 | 8/2013 |
| WO | WO/2013/169660 | 11/2013 |
| WO | WO/2013/169662 | 11/2013 |
| WO | WO/2015/050818 | 4/2015 |
| WO | WO/2015/050819 | 4/2015 |
| WO | WO/2015/050820 | 4/2015 |
| WO | WO/2015/050822 | 4/2015 |
| WO | WO/2015/100182 | 7/2015 |
| WO | WO/2015/100183 | 7/2015 |
| WO | WO/2015/100184 | 7/2015 |
| WO | WO/2015/103161 | 7/2015 |
| WO | WO/2015/1001811 | 7/2015 |
| WO | WO/2015/171408 | 12/2015 |
| WO | WO/2016/007525 | 1/2016 |
| WO | WO/2016/007529 | 1/2016 |
| WO | WO/2016/007531 | 1/2016 |
| WO | WO/2016/109257 | 7/2016 |
| WO | WO/2016/109288 | 7/2016 |
| WO | WO/2016/109289 | 7/2016 |
| WO | WO/2016/109290 | 7/2016 |
| WO | WO/2016/109291 | 7/2016 |
| WO | WO/2016/109300 | 7/2016 |
| WO | WO/2016/109301 | 7/2016 |
| WO | WO/2016/109302 | 7/2016 |
| WO | WO/2016/109303 | 7/2016 |
| WO | WO/2016/109304 | 7/2016 |
| WO | WO/2016/109305 | 7/2016 |
| WO | WO/2016/122802 | 8/2016 |

OTHER PUBLICATIONS

Shibata, et al., "UK-1, A Novel Cytotoxic Metabolite From *Streptomyces* sp. 517-02 II. Structural Eluciation", The Journal of Antibiotics, vol. 46, No. 7, pp. 1095-1100 (1993).

Shimano, et al., "Enantioselective Total Synthesis of the Antifungal Dilactone, UK-2A: The Determination of the Relative and Absolute Configurations", Tetrahedron Letters, vol. 39, pp. 4363-4366 (1998).

Shimano, et al., "Total Synthesis of the Antifungal Dilactones UK-2A and UK-3A: The Determination of their Relative and Absolute Configurations, Analog Synthesis and Antifungal Activities", Tetrahedron Letters, vol. 54, pp. 12745-12774 (1998).

Ueki, et al., "UK-1, A Novel Cytotoxic Metabolite from *Streptomyces* sp. 517-02 I. Taxonomy Fermentation, Isolation, Physico-Chemical and Biological Properites", The Journal of Antibiotics, vol. 50, No. 7, pp. 551-555 (1997).

Ueki, UK-2A, B, C and D, Novel Antifungal from *Streptomyces* sp. 517-02 I. Fermentation, Isolation and Biological Properties:, The Journal of Antibiotics, vol. 49, No. 7, pp. 639-643 (1996).

Ueki, et al., "UK-3A, A Novel Antifungal Antibiotic from *Streptomyces* sp. 517-02: Fermentation, Isolation, Structural Elucidation and Biological Properties":, The Journal of Antibiotics, vol. 50, No. 7, pp. 551-555 (1997).

Ueki, et al., "The Mode of Action of UK-2A and UK-3A, Novel Antifungal Antibiotics from *Streptomyces* sp. 517-02", The Journal of Antibiotics, vol. 50, No. 12, pp. 1052-1057 (1997).

Patent Abstracts of Japan vol. 1998, No. 06, Apr. 30, 1998 JP 10053583A (Mitsubishi Chem Corp) Feb. 24, 1998 abstract example 20.

Database Chemabs Online, Chemical Abstracts Service, Columbus, Ohio, US: accession No. CA63:16300d XP002164206.

International Search Authority, International Search Report and Written Opinion for PCT/US2005/028407, dated Aug. 5, 2015, 8 pages.

Thomas, S., International Search Report for PCT/US14/058067, dated Dec. 22, 2014, pp. 1-4, ISA/US.

Thomas, S., International Search Report for PCT/US14/058070, dated Dec. 15, 2014, pp. 1-4, ISA/US.

Thomas, S., Written Opinion for PCT/US14/058067, dated Dec. 22, 2014, pp. 1-5, ISA/US.

Thomas, S., Written Opinion for PCT/US14/058070, dated Dec. 15, 2014, pp. 1-5, ISA/US.

Anonymous, Synergistic Fungicidal Composition of Heterocyclic Aromatic Amides and Traizoles, ip.com Journal, ip.com, Electronic Publication, West Henrietta, NY, US Jul. 2004, 11 pages.

Backman, P., Fungicide Formulation: Relationship to Biological Activity, Ann. Rev. Phytophathol, 1978, 16, pp. 211-237.

BASF New Fungicide Xemium Got Full Approval in EU, Agronews, Jul. 18, 2012. Retrieved from the Internet: URL: http://news.agropages.com/News/NewsDetail---7386.htm, 1 page.

Bolton, M. et al., "Wheat leaf rust caused by *Puccinia triticina*," Molecular Plant Pathology, vol. 9, No. 5, 2008, pp. 563-575.

(56) References Cited

OTHER PUBLICATIONS

Davari, M. et al. "Quantum Chemical Investigation of Intramolecular Thione-Thiol Tautomerism of 1,2,4-triazole-3-thione and its disubstituted derivatives," Journal of Molecular Modeling, Sep. 2009, 16(5), pp. 841-855.
FRAC Code List: Fungicides Sorted by Mode of Action (including FRAC Code numbering), Fungicide REsistance Action Committee, Dec. 2008, 10 pages.
Fungicidal Mixtures, IP.com Prior Art Database Technical Disclosure, (Jul. 5, 2005), XP055073888, COI: http://ip.com/pdf/ipcompad/IPCOM000126160D.pdf, 12 pages.
Gisi, U., "Synergistic Interaction of Fungicides in Mixtures," The American Phytophathological Society, vol. 86, No. 11, 1996, pp. 1273-1279.
Hu, Z. et al., "Synthesis of Novel Analogues of Antimycin A3," Tetrahedron Letters 49 (2008), pp. 5192-5195.
Huang, C. et al., :"Synergistic Interactions between Chitinase ChiCW and Fungicides Against Plant Fungal Pathogens,": J. Microbiol. Biotechnol., 2008, 18(4), pp. 784-787.
Kissling, E., "Crop Protection Pipeline Value Jumps to Euro 2.4 Billion," BASF SE, Mar. 10, 2011, Retrieved from the internet:, URL:http://agro.basf.com/agri/AP-Internet/en/content/news_room/news/basf-crop-protection-pipleine-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Jul. 2008, pp. 84-87.
Ueki, M., et al., "Uk-2A, B, C, and D, Novel Antifungal Antibiotics from *Streptomyces* sp. 517-02 I. Fermentation, Isolation, and Biological Properties," The Journal of Antibiotics, vol. 49, No. 87, Jul. 1996, pp. 639-643.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals,": Applied and Environmental Microbiology, vol. 77, No. 4, Feb. 2011, pp. 1460-1465.
PubChem: Open Chemistry Database, Substance Record for SID 74383515. Deposit Date Jun. 11, 2009. Retrieved from the Internet <URL:https://pubchem.ncbi.nlm.nih.gov/sustance/74383515#section=Top>, 5 pages.
Science for a Better Life, Bayer CropScience "positioned for Growth." Jun. 2008, 22 pages.
Calcium Dodecyl Benzene Sulfonate, CAS 26264-06-2, (http://www.hichem.com/product/showproduct.php?id=334639) Mar. 28, 2013, 4 pages.
Tani, K. et al., The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruitcola and Botrytis cinerea," 1987, Plant Disease, vol. 71, No. 4, pp. 316-319.
Written Opinion and Search Report for PCT Patent Application No. PCT/US2015/067115 dated Mar. 11, 2016, 7 pages.
Gerald R. Stephenson, Ian G. Ferris, Patrick T. Holland, and Monica Nordberg, "Glossary of Terms Relating to Pesticides," in Pure and Applied Chemistry 2006, 78 (11), 2075-2154; International Union of Pure and Applied Chemistry.
D. J. Chitwood, "Nematicides," in Encyclopedia of Agrochemicals (3), pp. 1104-1115, John Wiley & Sons, New York, NY, 2003; http://naldc.nal.usda.gov/download/43874/PDF.

* cited by examiner

THIOPICOLINAMIDE COMPOUNDS WITH FUNGICIDAL ACTIVITY

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to thiopicolinamides and their use as fungicides. The compounds of the present disclosure may offer protection against ascomycetes, basidiomycetes, deuteromycetes and oomycetes.

One embodiment of the present disclosure may include compounds of Formula I:

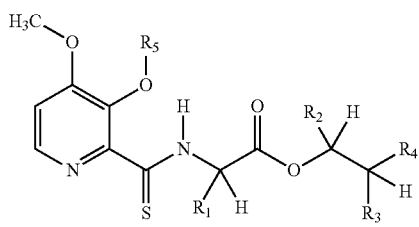

I in which:
$R_1$ is hydrogen or $C_1$-$C_5$ alkyl, substituted with 0, 1 or multiple $R_6$;
$R_2$ is hydrogen, $C_1$-$C_5$ alkyl or cycloalkyl, each optionally substituted with 0, 1 or multiple $R_6$;
$R_3$ is chosen from alkyl, cycloalkyl, alkenyl, aryl or heteroaryl, each optionally substituted with 0, 1 or multiple $R_6$;
$R_4$ is chosen from alkyl, cycloalkyl, alkenyl, aryl, heteroaryl, alkoxy, aryloxy, heteroaryloxy, each optionally substituted with 0, 1 or multiple $R_6$;
$R_5$ is chosen from hydrogen, —C(O)$R_7$, or —CH$_2$OC(O)$R_7$
$R_6$ is chosen from hydrogen, alkyl, aryl, acyl, halo, alkenyl, alkynyl, alkoxy, cyano or heterocyclyl, each optionally substituted with 0, 1 or multiple $R_8$;
$R_7$ is chosen from from alkyl, alkoxy, or aryl, each substituted with 0, 1 or multiple $R_6$;
$R_8$ is chosen from hydrogen, alkyl, aryl, acyl, halo, alkenyl, alkoxy, or heterocyclyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl, and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl, and the like.

The terms "aryl" and "Ar" refer to any aromatic ring, mono- or bi-cyclic, containing 0 heteroatoms.

The term "heterocyclyl" refers to any aromatic or non-aromatic ring, mono- or bi-cyclic, containing one or more heteroatoms.

The term "alkoxy" refers to an —OR substituent.
The term "acyloxy" refers to an —OC(O)R substituent.
The term "cyano" refers to a —C≡N substituent.
The term "hydroxyl" refers to an —OH substituent.
The term "amino" refers to a —N(R)$_2$ substituent.
The term "arylalkoxy" refers to —O(CH$_2$)$_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —NO$_2$ substituent.
The term thioalkyl refers to an —SR substituent.

Throughout the disclosure, reference to the compounds of Formula I is read as also including all stereoisomers, for example diastereomers, enantiomers, and mixtures thereof. In another embodiment, Formula I is read as also including salts or hydrates thereof. Exemplary salts include, but are not limited to: hydrochloride, hydrobromide, hydroiodide, trifluoroacetate, and trifluoromethane sulfonate.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendable, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting, and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzovindiflupyr, benzylaminobenzene-sulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), coumoxystrobin, cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dipymetitrone, dithianon, dodemorph, dodemorph acetate, dodine, dodine free base, edifenphos, enestrobin, enestroburin, enoxastrobin, epoxiconazole, ethaboxam, ethoxyquin, etridiazole, famoxadone, fenamidone, fenaminostrobin, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flufenoxystrobin, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isofetamid, isoprothiolane, isopyrazam, isotianil, kasugamycin, kasugamycin hydrochloride hydrate, kresoxim-methyl, laminarin, mancopper, mancozeb, mandestrobin, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxathiapiprolin, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picarbutrazox, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyraziflumid, pyrazophos, pyribencarb, pyributicarb, pyrifenox, pyrimethanil, pyriofenone, pyrisoxazole, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolprocarb, tolylfluanid, triadimefon, triadimenol, triazoxide, triclopyricarb, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril, benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb, prothiocarb hydrochloride, pyracarbolid, pyridinitril, pyroxychlor, pyroxyfur, quinacetol, quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, afidopyropen, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, broflanilide, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, clacyfos, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclaniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicloromezotiaz, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepallethrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flometoquin, flonicamid, flubendiamide, flucofuron, flucycloxuron, flucythrinate, flufenerim, flufenoxuron, flufenprox, flufiprole, fluhexafon, flupyradifurone, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptafluthrin, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kappa-bifenthrin, kappa-tefluthrin, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, momfluorothrin, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyflubumide, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyriminostrobin, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, tetraniliprole, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tioxazafen, tolfenpyrad, tralomethrin, transfluthrin, transpermethrin, triarathene, triazamate, triazophos, trichlorfon, trichlormetaphos-3, trichloronat, trifenofos, triflumezopyrim, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclopyrimorate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenquinotrione, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-P, glyphosate, halauxifen, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, napropamide-M, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiafenacil, tiocarbazil, tioclorim, tolpyralate, topramezone, tralkoxydim, triafamone, tri-allate, triasulfuron, triaziflam, tribenuron, tricamba, triclopyr, tridiphane, trietazine, trifloxysulfuron, trifludimoxazin, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those skilled in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Zymoseptoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Pyricularia oryzae*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Colletotrichum lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, g/m$^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating thiopicolinamide compounds of Formula I. The following descriptions and examples are provided for illustrative purposes and should not be construed as limiting in terms of substituents or substitution patterns.

Compounds of Formula I wherein $R_1$, $R_2$, $R_3$, $R_4$ and $R_5$ are as originally defined, can be prepared according to the methods outlined in Scheme 1, steps a and b. Compounds of Formula 1.0 wherein $R_1$, $R_2$, $R_3$ and $R_4$ are as originally defined, can be prepared as described by the procedures outlined in US patent applications WO 2016/109289, WO 2016/109300, WO 2016/109257, WO 2016/109302 and WO 2016/109304. Compounds of Formula 1.0 can be treated with a thionating reagent such as phosphorus pentasulfide, an additive, such as hexamethyldisiloxane, optionally in a polar aprotic solvent such as acetonitrile ($CH_3CN$), at a temperature of about 0° C. to 80° C. to afford compounds of Formula 1.1, wherein $R_1$, $R_2$, $R_3$ and $R_4$ are as originally defined, as shown in a. It will be understood by those skilled in the art that compounds such as Formula 1.1 may also be prepared using other thionating agents including, but not limited to: sulfur, sulfhydric acid, sodium sulfide, sodium hydrosulfide, boron trisulfide, bis(diethylaluminum)sulfide, ammonium sulfide, Lawesson's reagent, ammonium O,O'-diethyl dithiophosphate, rhodanine, or a polymer supported thionating reagent. Additives can include, but not limited to, aluminum oxide ($Al_2O_3$); inorganic bases, such as potassium carbonate and sodium bicarbonate; organic bases, such as triethylamine, diethylaniline, pyridine and morpholine. Optional solvents can include, but not limited to, aliphatic, alicyclic or aromatic hydrocarbons, such as hexane, cyclohexane or toluene; halogenated hydrocarbons, such as dichloromethane, 1,2-dichloroethane and chlorobenzene; ethers, such as diethyl ether, 1,4-dioxane, THF and 1,2-dimethoxyethane; and other polar aprotic solvents such as pyridine and hexamethylphosphoramide (HMPA). In step b, treatment of compounds of Formula 1.1, wherein $R_1$, $R_2$, $R_3$ and $R_4$ are as originally defined, with an appropriate alkyl halide with or without a reagent such as sodium iodide (NaI) and an alkali carbonate base, such as sodium carbonate ($Na_2CO_3$) or potassium carbonate ($K_2CO_3$), in a solvent like acetone at a temperature of about 55° C., or by treatment with an acyl halide or anhydride in the presence of an amine base, such as pyridine, triethylamine ($Et_3N$), DMAP, or mixtures thereof, in an optional aprotic solvent such as DCM, at a temperature of about 23° C., to afford compounds of Formula I wherein $R_1$, $R_2$, $R_3$, $R_4$ and $R_5$ are as originally defined.

Scheme 1

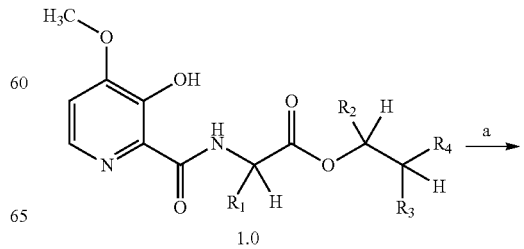

1.0

-continued

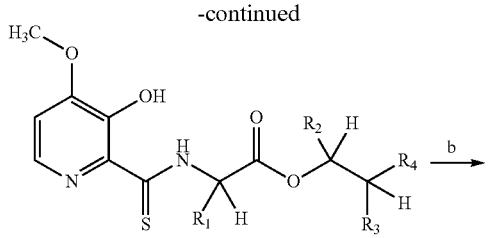

1.1

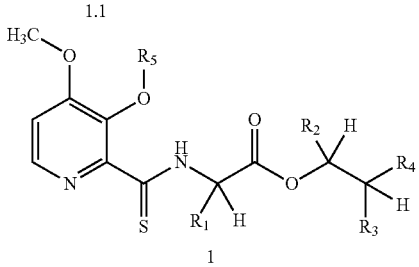

1

EXAMPLES

Example 1

Preparation of (1R,2S)-1-(2-chlorophenoxy)-1-phenylpropan-2-yl (3-hydroxy-4-methoxypyridine-2-carbonothioyl)-L-alaninate. Compound 22

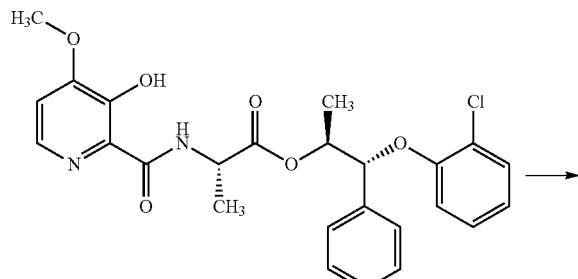

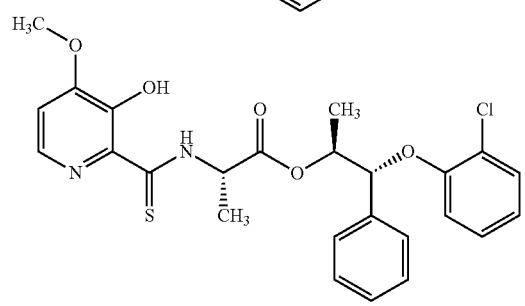

To a solution of (1R,2S)-1-(2-chlorophenoxy)-1-phenylpropan-2-yl (3-hydroxy-4-methoxypicolinoyl)-L-alaninate (WO 2016/109304) (0.100 g, 0.206 mmol) in acetonitrile (1 ml) was added phosphorus pentasulfide (0.092 g, 0.412 mmol) and 1,1,1,3,3,3-hexamethyldisiloxane (0.220 ml, 1.031 mmol). The mixture was heated at 45° C. for 30 min. The mixture was diluted with EtOAc (10 mL) and the reaction was quenched with NaHCO₃ (10 mL). The organic phase was shaken and separated and the products extracted with EtOAc (2×10 mL). The combined organics were passed through a phase separator and concentrated under reduced pressure. The crude residue was purified via flash chromatography (4 g silica column) using a 5-60% acetone/hexanes mixture as the eluent to provide the title compound (83 mg, 0.166 mmol, 80% yield) as a yellow foam. $^1$H NMR (400 MHz, CDCl₃) δ 12.83 (s, 1H), 10.62 (d, J=7.5 Hz, 1H), 7.95 (d, J=5.1 Hz, 1H), 7.45-7.38 (m, 2H), 7.37-7.28 (m, 4H), 6.99 (ddd, J=8.3, 7.5, 1.7 Hz, 1H), 6.86 (d, J=5.1 Hz, 1H), 6.81 (td, J=7.7, 1.4 Hz, 1H), 6.65 (dd, J=8.4, 1.5 Hz, 1H), 5.42-5.35 (m, 1H), 5.29 (d, J=4.8 Hz, 1H), 5.03 (p, J=7.2 Hz, 1H), 3.95 (d, J=2.8 Hz, 3H), 1.46 (d, J=6.4 Hz, 3H), 1.42 (d, J=7.2 Hz, 3H). IR (thin film) 2937, 1735, 1512, 1481, 1274, 1245, 1201, 1059, 728 cm⁻¹. HRMS-ESI (m/z) ([M+H]+) calcd for $C_{25}H_{26}ClN_2O_5S$, 501.1245; found, 501.1272.

Example 2

Preparation of (1R,2S)-1-(2-chlorophenoxy)-1-phenylpropan-2-yl (3-acetoxy-4-methoxypyridine-2-carbonothioyl)-L-alaninate. Compound 57

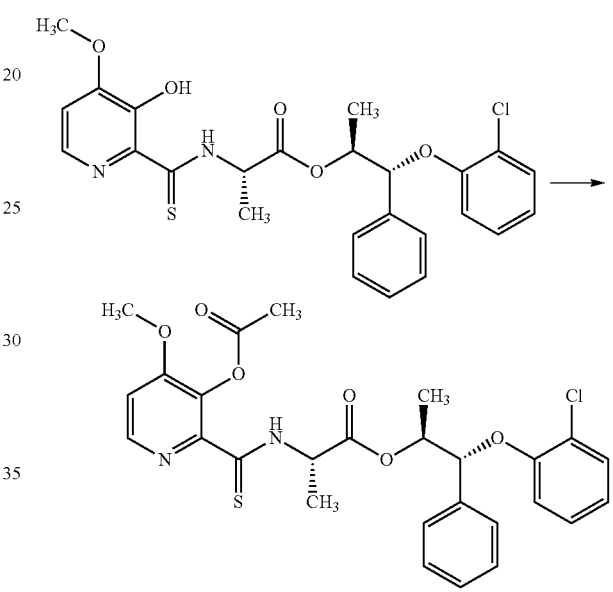

To a stirred solution of (1R,2S)-1-(2-chlorophenoxy)-1-phenylpropan-2-yl (3-hydroxy-4-methoxypyridine-2-carbonothioyl)-L-alaninate (Compound 22) (0.066 g, 0.132 mmol) in pyridine (0.5 mL, 6.21 mmol) was added acetic anhydride (0.5 mL, 5.30 mmol). The mixture was stirred at room temperature for 30 min. The mixture was then concentrated under reduced pressure. The residue was purified via flash chromatography (4 g silica column) using a 5-60% acetone/hexanes mixture as the eluent to provide the title compound (54 mg; 75%) as a yellow foam. $^1$H NMR (400 MHz, CDCl₃) δ 9.86 (d, J=7.2 Hz, 1H), 8.28 (dd, J=5.4, 0.9 Hz, 1H), 7.45-7.37 (m, 2H), 7.36-7.27 (m, 4H), 7.02-6.93 (m, 2H), 6.81 (td, J=7.6, 1.4 Hz, 1H), 6.67 (dd, J=8.3, 1.4 Hz, 1H), 5.41-5.32 (m, 1H), 5.28 (d, J=4.8 Hz, 1H), 5.13 (p, J=7.1 Hz, 1H), 3.89 (s, 3H), 2.34 (s, 3H), 1.46 (d, J=6.4 Hz, 3H), 1.35 (d, J=7.2 Hz, 3H). IR (thin film) 2983, 1768, 1739, 1481, 1192, 1175, 731 cm⁻¹. HRMS-ESI (m/z) ([M+H]+) calcd for $C_{27}H_{28}ClN_2O_6S$, 543.1351; found, 543.1382.

Compounds of the present disclosure, their preparation method, and appearance are shown below in Table 1. Analytical data for the compounds shown in Table 1 is shown in Table 2 below.

Example A

Evaluation of Fungicidal Activity: Leaf Blotch of Wheat (*Zymoseptoria Tritici*; Bayer Code SEPTTR)

Technical grades of materials were dissolved in acetone, which were then mixed with nine volumes of water (H₂O)

containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases, unless stated otherwise. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of Zymoseptoria tritici either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the 1st leaves of untreated plants, infection levels were assessed on a scale of 0 to 100 percent disease severity. Percent disease control was calculated using the ratio of disease severity on treated plants relative to untreated plants. The results of the evaluation are shown below in Table 4.

Example B

Evaluation of Fungicidal Activity: Wheat Brown Rust (*Puccinia Triticina*; Synonym: *Puccinia recondita* f. Sp. *Tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A. The results of the evaluation are shown below in Table 4.

Example C

Evaluation of Fungicidal Activity: Asian Soybean Rust (*Phakopsora pachyrhizi*; Bayer Code PHAKPA)

Technical grades of materials were dissolved in acetone, which were then mixed with nine volumes of $H_2O$ containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% relative humidity then transferred to a growth room at 23° C. for disease to develop. Disease severity was assessed on the sprayed leaves. The results of the evaluation are shown below in Table 5.

TABLE 1

Compound Structure, Preparation Method, and Appearance

| Cmpd. No. | Structure | As Prepared According To | Appearance |
|---|---|---|---|
| 1 | 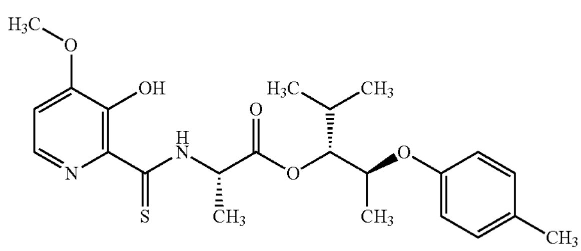 [SMILES: COc1ccnc(C(=S)N[C@@H](C)C(=O)O[C@H](C(C)C)[C@H](C)Oc2ccc(C)cc2)c1O] | WO 2016/109302 Example 1 | Yellow Semi-Solid |
| 2 | 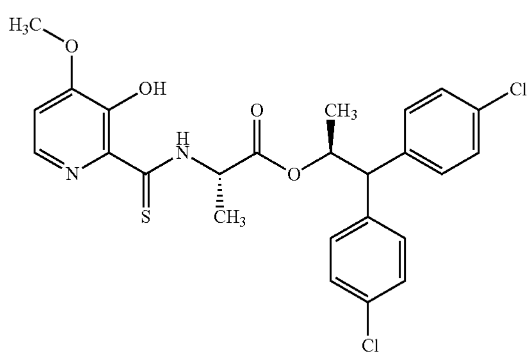 [SMILES: COc1ccnc(C(=S)N[C@@H](C)C(=O)O[C@@H](C)C(c2ccc(Cl)cc2)c2ccc(Cl)cc2)c1O] | WO 2016/109257 Example 1 | Yellow Foam |

TABLE 1-continued

Compound Structure, Preparation Method, and Appearance

| Cmpd. No. | Structure | As Prepared According To | Appearance |
|---|---|---|---|
| 3 | 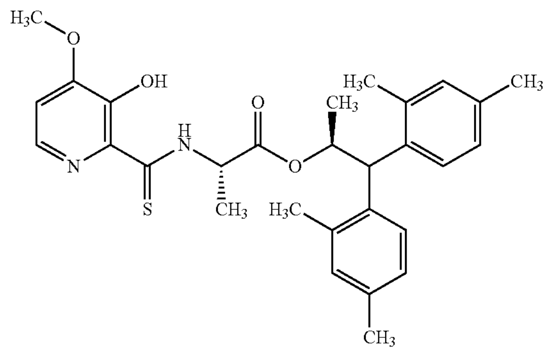 [SMILES: COc1ccnc(C(=S)N[C@@H](C)C(=O)O[C@@H](C)C(c2ccc(C)cc2C)c2ccc(C)cc2C)c1O] | WO 2016/109257 Example 1 | Yellow Wax |
| 4 | 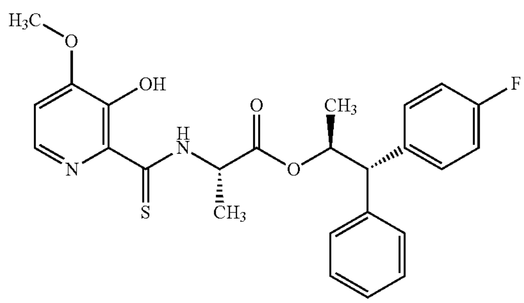 [SMILES: COc1ccnc(C(=S)N[C@@H](C)C(=O)O[C@@H](C)[C@@H](c2ccccc2)c2ccc(F)cc2)c1O] | WO 2016/109257 Example 1 | Yellow Semi-Solid |
| 5 | 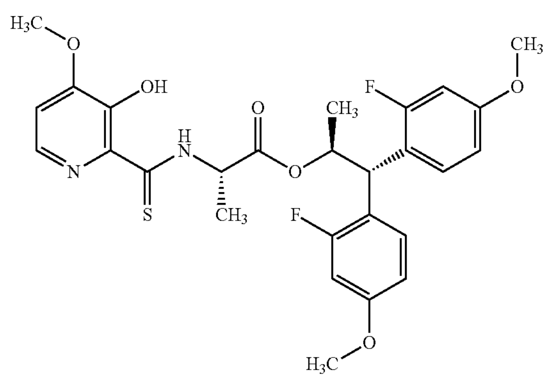 | WO 2016/109257 Example 1 | Yellow Wax |
| 6 | 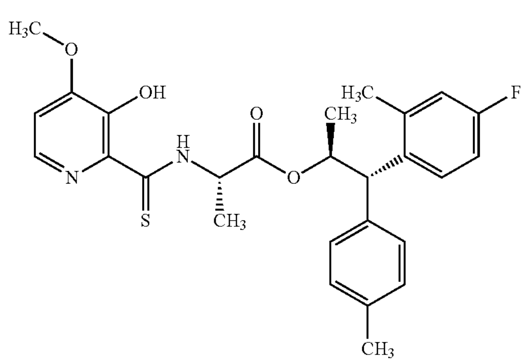 [SMILES: COc1ccnc(C(=S)N[C@@H](C)C(=O)O[C@@H](C)[C@@H](c2ccc(C)cc2)c2ccc(F)cc2C)c1O] | WO 2016/109257 Example 1 | Yellow Solid |

TABLE 1-continued

Compound Structure, Preparation Method, and Appearance

| Cmpd. No. | Structure | As Prepared According To | Appearance |
|---|---|---|---|
| 7 | 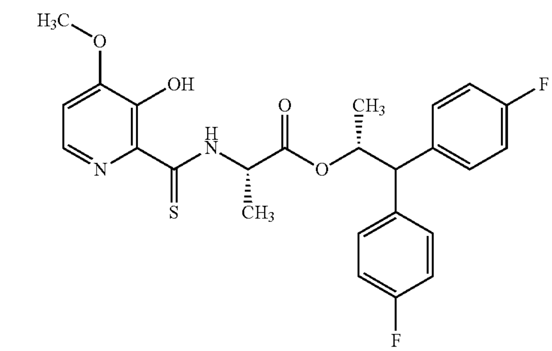 [SMILES: COc1ccnc(C(=S)N[C@@H](C)C(=O)O[C@H](C)C(c2ccc(F)cc2)c2ccc(F)cc2)c1O] | WO 2016/109257 Example 1 | Yellow Solid |
| 8 | 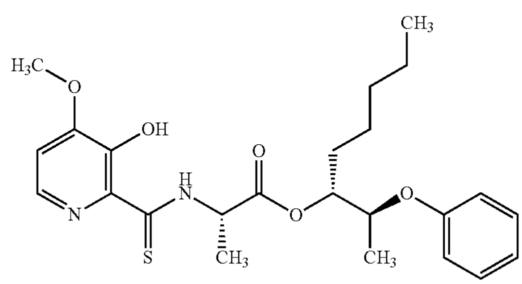 [SMILES: CCCCC[C@@H](OC(=O)[C@H](C)NC(=S)c1nccc(OC)c1O)[C@H](C)Oc1ccccc1] | WO 2016/109302 Example 1 | Yellow Solid |
| 9 | 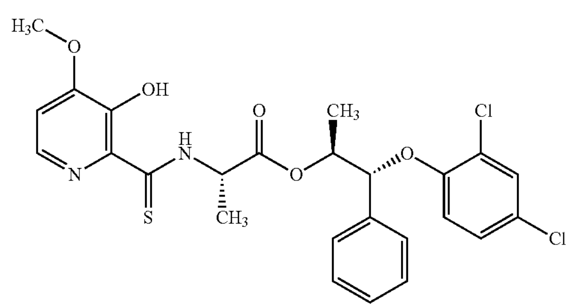 [SMILES: COc1ccnc(C(=S)N[C@@H](C)C(=O)O[C@@H](C)[C@H](Oc2ccc(Cl)cc2Cl)c2ccccc2)c1O] | WO 2016/109304 Example 1 | Yellow Foam |
| 10 | 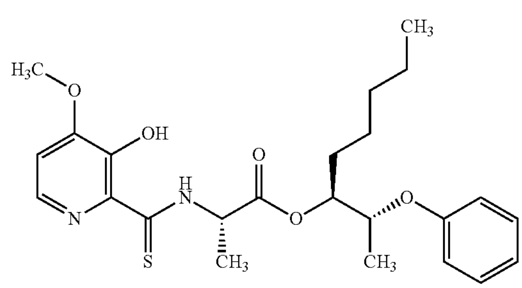 [SMILES: CCCCC[C@H](OC(=O)[C@H](C)NC(=S)c1nccc(OC)c1O)[C@@H](C)Oc1ccccc1] | WO 2016/109302 Example 1 | Orange Wax |
| 11 | 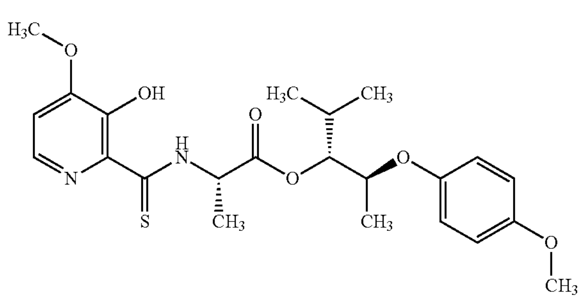 [SMILES: COc1ccc(O[C@@H](C)[C@H](OC(=O)[C@H](C)NC(=S)c2nccc(OC)c2O)C(C)C)cc1] | WO 2016/109302 Example 1 | Yellow Solid |

TABLE 1-continued

Compound Structure, Preparation Method, and Appearance

| Cmpd. No. | Structure | As Prepared According To | Appearance |
|---|---|---|---|
| 12 | 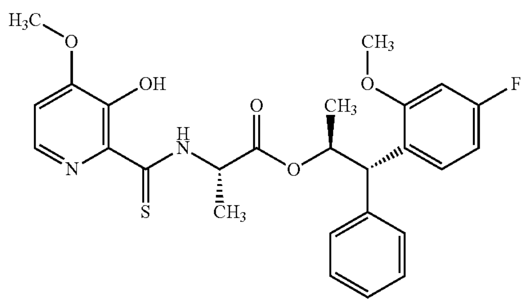 [SMILES: COc1cc(F)ccc1[C@H](c1ccccc1)[C@H](C)OC(=O)[C@H](C)NC(=S)c1nccc(OC)c1O] | WO 2016/109257 Example 1 | Orange Solid |
| 13 | 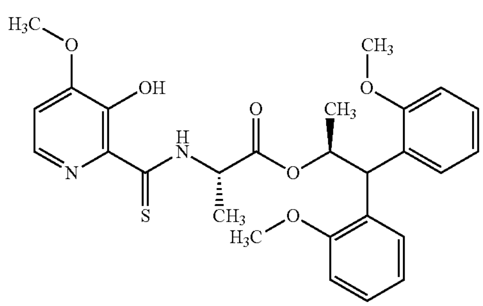 [SMILES: COc1ccccc1C(c1ccccc1OC)[C@H](C)OC(=O)[C@H](C)NC(=S)c1nccc(OC)c1O] | WO 2016/109257 Example 1 | Yellow Solid |
| 14 | 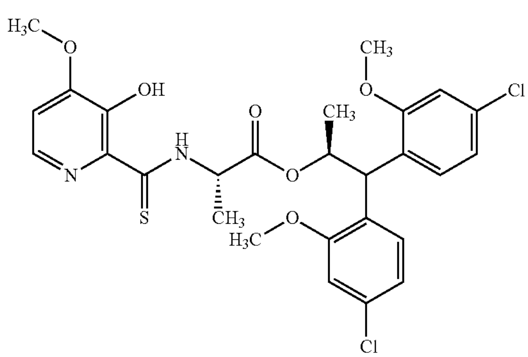 [SMILES: COc1cc(Cl)ccc1C(c1ccc(Cl)cc1OC)[C@H](C)OC(=O)[C@H](C)NC(=S)c1nccc(OC)c1O] | WO 2016/109257 Example 1 | Yellow Wax |
| 15 | 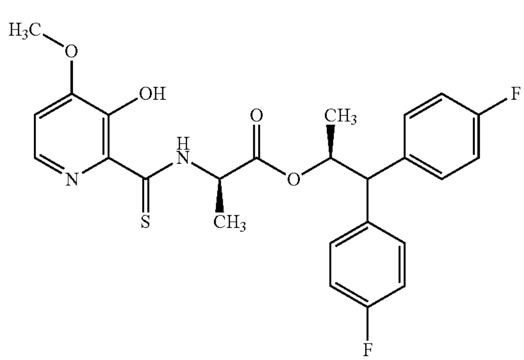 [SMILES: COc1ccnc(C(=S)N[C@H](C)C(=O)O[C@@H](C)C(c2ccc(F)cc2)c2ccc(F)cc2)c1O] | WO 2016/109257 Example 1 | Yellow Foam |

TABLE 1-continued

Compound Structure, Preparation Method, and Appearance

| Cmpd. No. | Structure | As Prepared According To | Appearance |
|---|---|---|---|
| 16 | 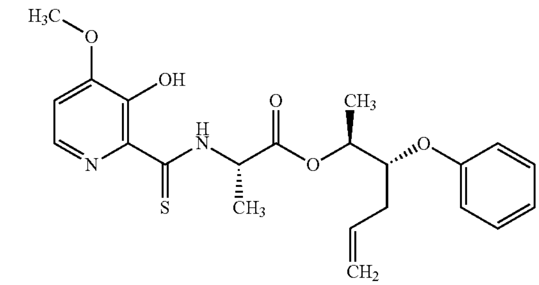 [SMILES: C=CC[C@@H](Oc1ccccc1)[C@H](C)OC(=O)[C@H](C)NC(=S)c1nccc(OC)c1O] | WO 2016/109289 Example 1 | Yellow Solid |
| 17 | 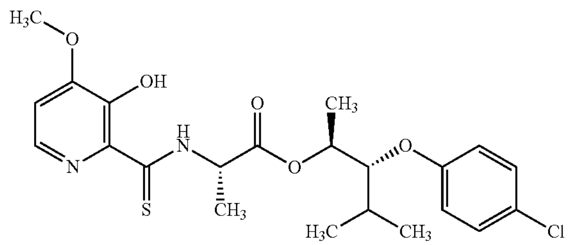 [SMILES: COc1ccnc(C(=S)N[C@@H](C)C(=O)O[C@@H](C)[C@H](Oc2ccc(Cl)cc2)C(C)C)c1O] | WO 2016/109289 Example 1 | Yellow Solid |
| 18 | 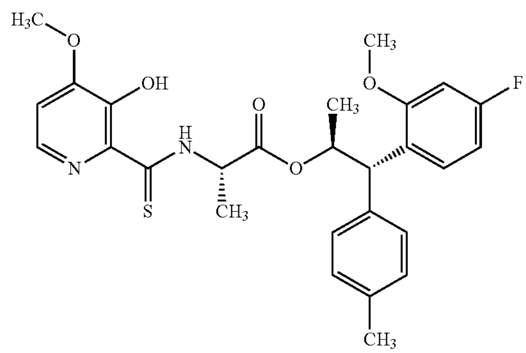 [SMILES: COc1cc(F)ccc1[C@H](c1ccc(C)cc1)[C@H](C)OC(=O)[C@H](C)NC(=S)c1nccc(OC)c1O] | WO 2016/109257 Example 1 | Yellow Foam |
| 19 | 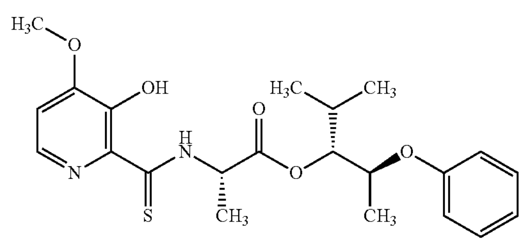 [SMILES: COc1ccnc(C(=S)N[C@@H](C)C(=O)O[C@H](C(C)C)[C@H](C)Oc2ccccc2)c1O] | WO 2016/109302 Example 1 | Yellow Solid |
| 20 | 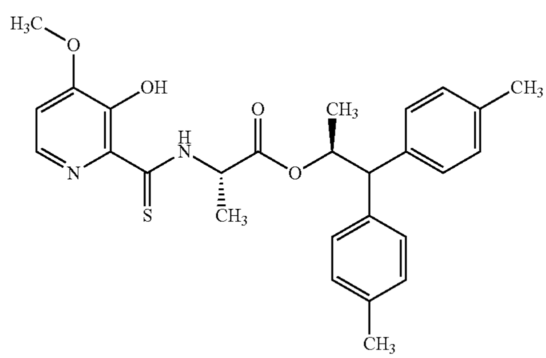 [SMILES: COc1ccnc(C(=S)N[C@@H](C)C(=O)O[C@@H](C)C(c2ccc(C)cc2)c2ccc(C)cc2)c1O] | WO 2016/109257 Example 1 | Yellow Wax |

TABLE 1-continued

Compound Structure, Preparation Method, and Appearance

| Cmpd. No. | Structure | As Prepared According To | Appearance |
|---|---|---|---|
| 21 | 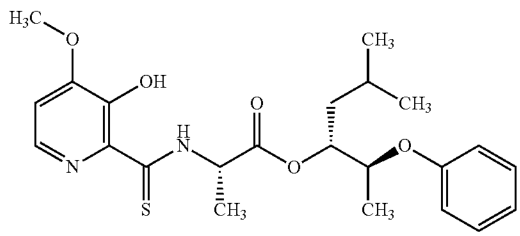 [SMILES: COc1ccnc(C(=S)N[C@@H](C)C(=O)O[C@H](CC(C)C)[C@H](C)Oc2ccccc2)c1O] | WO 2016/109302 Example 1 | Orange Wax |
| 22 | 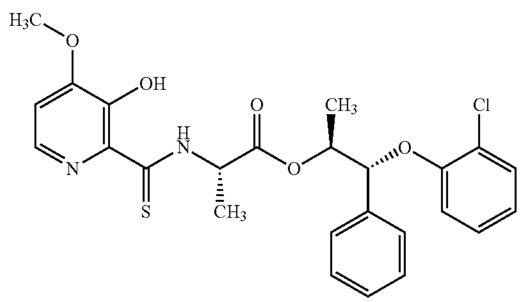 [SMILES: COc1ccnc(C(=S)N[C@@H](C)C(=O)O[C@@H](C)[C@H](Oc2ccccc2Cl)c2ccccc2)c1O] | WO 2016/109304 Example 1 | Yellow Foam |
| 23 | 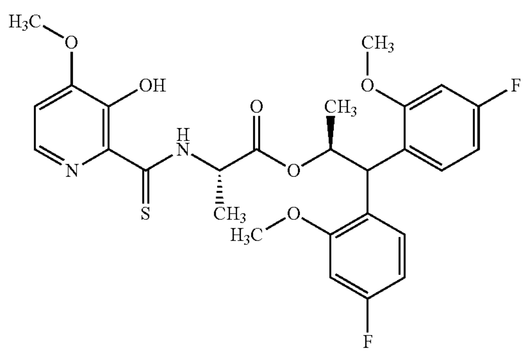 [SMILES: COc1cc(F)ccc1C(c1ccc(F)cc1OC)[C@H](C)OC(=O)[C@H](C)NC(=S)c1nccc(OC)c1O] | WO 2016/109257 Example 1 | Yellow Solid |
| 24 | 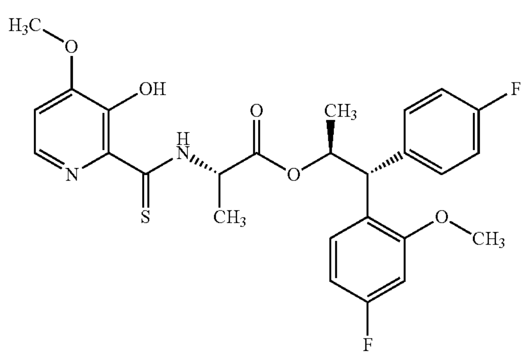 [SMILES: COc1cc(F)ccc1[C@@H](c1ccc(F)cc1)[C@H](C)OC(=O)[C@H](C)NC(=S)c1nccc(OC)c1O] | WO 2016/109257 Example 1 | Yellow Solid |
| 25 | 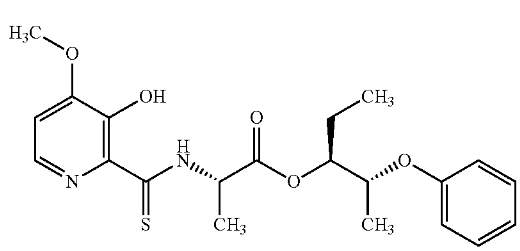 [SMILES: CC[C@H](OC(=O)[C@H](C)NC(=S)c1nccc(OC)c1O)[C@@H](C)Oc1ccccc1] | WO 2016/109302 Example 1 | Yellow Solid |

TABLE 1-continued

Compound Structure, Preparation Method, and Appearance

| Cmpd. No. | Structure | As Prepared According To | Appearance |
|---|---|---|---|
| 26 | 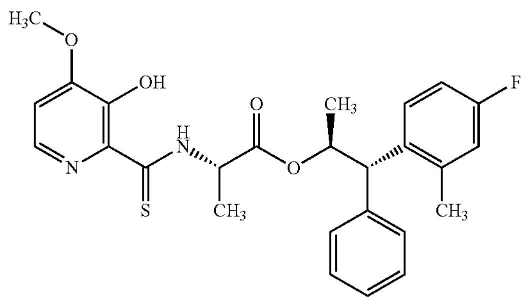 [SMILES: COc1ccnc(C(=S)N[C@@H](C)C(=O)O[C@@H](C)[C@@H](c2ccccc2)c2ccc(F)cc2C)c1O] | WO 2016/109257 Example 1 | Yellow Solid |
| 27 | 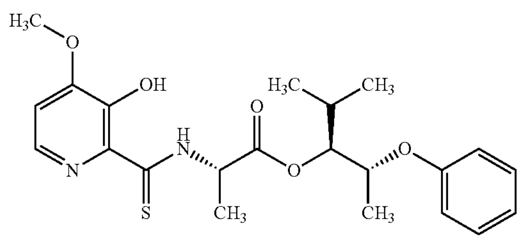 [SMILES: COc1ccnc(C(=S)N[C@@H](C)C(=O)O[C@@H](C(C)C)[C@@H](C)Oc2ccccc2)c1O] | WO 2016/109302 Example 1 | Yellow Solid |
| 28 | 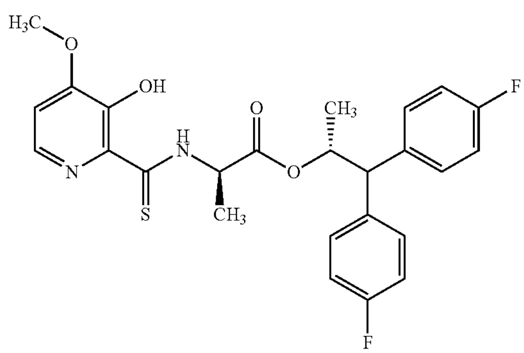 [SMILES: COc1ccnc(C(=S)N[C@H](C)C(=O)O[C@H](C)C(c2ccc(F)cc2)c2ccc(F)cc2)c1O] | WO 2016/109257 Example 1 | Yellow Solid |
| 29 | 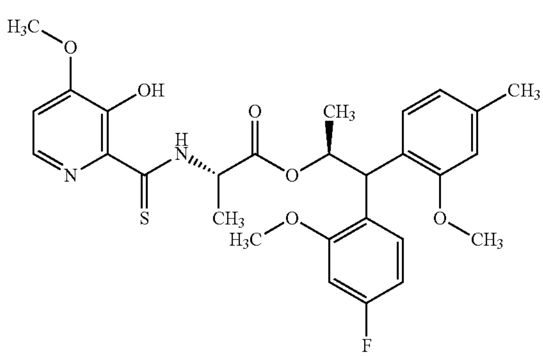 [SMILES: COc1cc(C)ccc1C(c1ccc(F)cc1OC)[C@H](C)OC(=O)[C@H](C)NC(=S)c1nccc(OC)c1O] | WO 2016/109257 Example 1 | Yellow Solid |

TABLE 1-continued

Compound Structure, Preparation Method, and Appearance

| Cmpd. No. | Structure | As Prepared According To | Appearance |
|---|---|---|---|
| 30 | 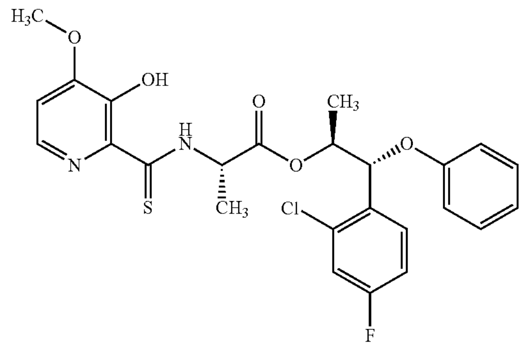 [SMILES: COc1ccnc(C(=S)N[C@@H](C)C(=O)O[C@@H](C)[C@H](Oc2ccccc2)c2ccc(F)cc2Cl)c1O] | WO 2016/109304 Example 1 | Yellow Solid |
| 31 | 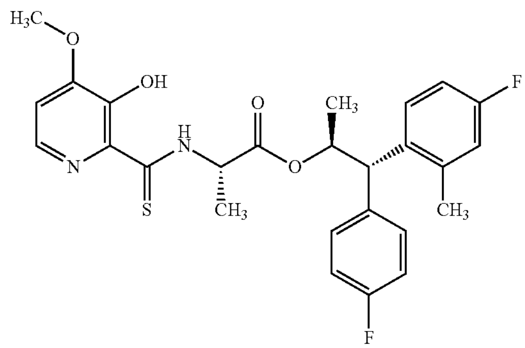 [SMILES: COc1ccnc(C(=S)N[C@@H](C)C(=O)O[C@@H](C)[C@@H](c2ccc(F)cc2)c2ccc(F)cc2C)c1O] | WO 2016/109257 Example 1 | Yellow Solid |
| 32 | 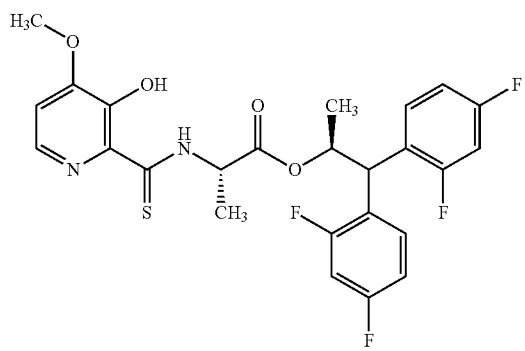 [SMILES: COc1ccnc(C(=S)N[C@@H](C)C(=O)O[C@@H](C)C(c2ccc(F)cc2F)c2ccc(F)cc2F)c1O] | WO 2016/109257 Example 1 | Yellow Solid |
| 33 | 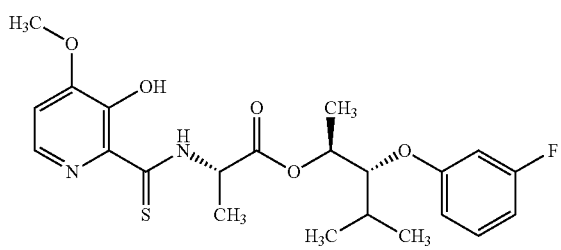 [SMILES: COc1ccnc(C(=S)N[C@@H](C)C(=O)O[C@@H](C)[C@H](Oc2cccc(F)c2)C(C)C)c1O] | WO 2016/109289 Example 1 | Yellow Solid |
| 34 | 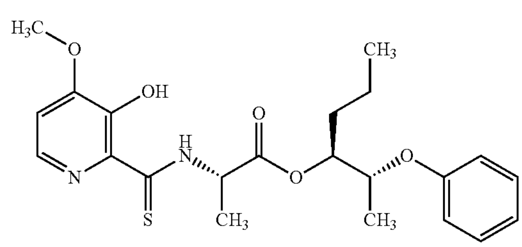 [SMILES: CCC[C@H](OC(=O)[C@H](C)NC(=S)c1nccc(OC)c1O)[C@@H](C)Oc1ccccc1] | WO 2016/109302 Example 1 | Yellow Oil |

TABLE 1-continued

Compound Structure, Preparation Method, and Appearance

| Cmpd. No. | Structure | As Prepared According To | Appearance |
|---|---|---|---|
| 35 | 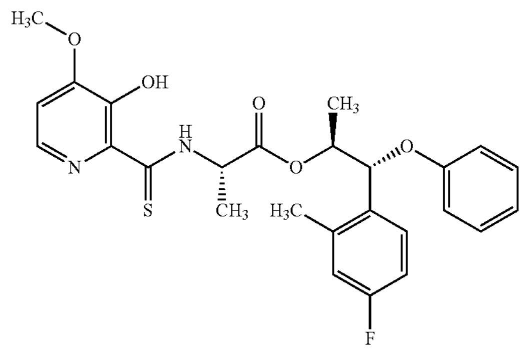 [SMILES: COc1ccnc(C(=S)N[C@@H](C)C(=O)O[C@@H](C)[C@H](Oc2ccccc2)c2ccc(F)cc2C)c1O] | WO 2016/109304 Example 1 | Yellow Solid |
| 36 | 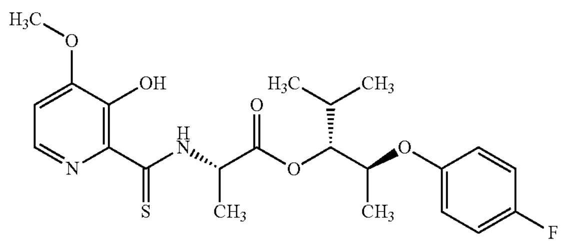 [SMILES: COc1ccnc(C(=S)N[C@@H](C)C(=O)O[C@H](C(C)C)[C@H](C)Oc2ccc(F)cc2)c1O] | WO 2016/109302 Example 1 | Yellow Solid |
| 37 | 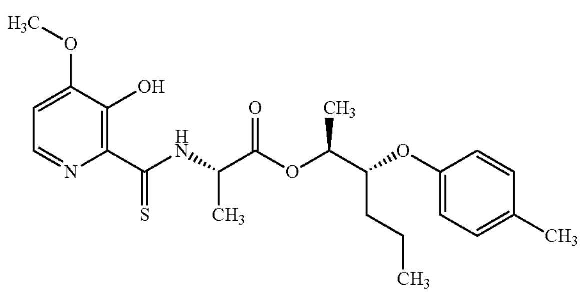 [SMILES: CCC[C@@H](Oc1ccc(C)cc1)[C@H](C)OC(=O)[C@H](C)NC(=S)c1nccc(OC)c1O] | WO 2016/109289 Example 1 | Yellow Solid |
| 38 | 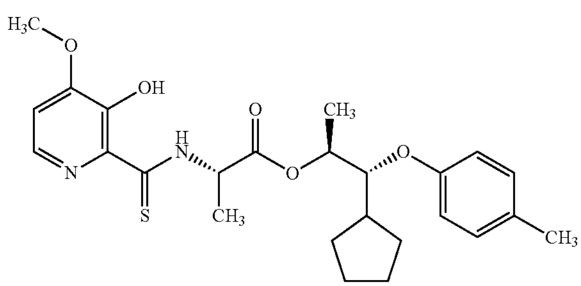 [SMILES: COc1ccnc(C(=S)N[C@@H](C)C(=O)O[C@@H](C)[C@H](Oc2ccc(C)cc2)C2CCCC2)c1O] | WO 2016/109289 Example 1 | Yellow Solid |
| 39 | 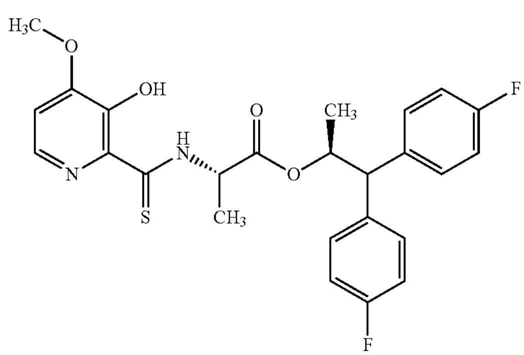 [SMILES: COc1ccnc(C(=S)N[C@@H](C)C(=O)O[C@@H](C)C(c2ccc(F)cc2)c2ccc(F)cc2)c1O] | WO 2016/109257 Example 1 | Yellow Foam |

TABLE 1-continued

Compound Structure, Preparation Method, and Appearance

| Cmpd. No. | Structure | As Prepared According To | Appearance |
|---|---|---|---|
| 40 | 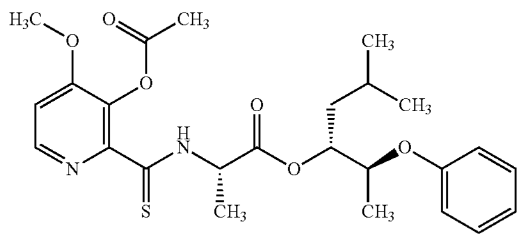 [SMILES: COc1ccnc(C(=S)N[C@@H](C)C(=O)O[C@H](CC(C)C)[C@H](C)Oc2ccccc2)c1OC(C)=O] | WO 2016/109302 Example 1, 2 | Red Wax |
| 41 | 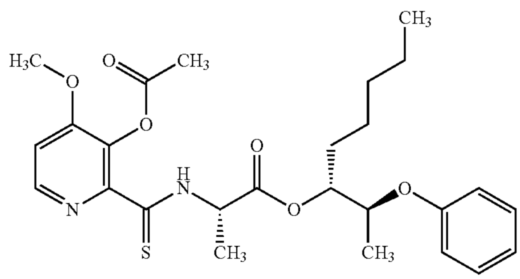 [SMILES: CCCCC[C@@H](OC(=O)[C@H](C)NC(=S)c1nccc(OC)c1OC(C)=O)[C@H](C)Oc1ccccc1] | WO 2016/109302 Example 1, 2 | Orange Wax |
| 42 | 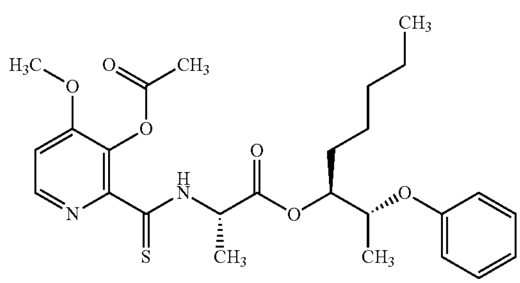 [SMILES: CCCCC[C@H](OC(=O)[C@H](C)NC(=S)c1nccc(OC)c1OC(C)=O)[C@@H](C)Oc1ccccc1] | WO 2016/109302 Example 1, 2 | Red Wax |
| 43 | 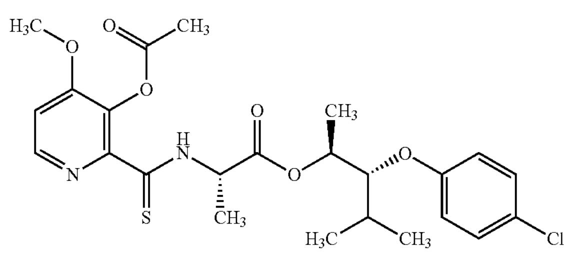 [SMILES: COc1ccnc(C(=S)N[C@@H](C)C(=O)O[C@@H](C)[C@H](Oc2ccc(Cl)cc2)C(C)C)c1OC(C)=O] | WO 2016/109289 Example 1, 2 | Brown Foam |
| 44 | 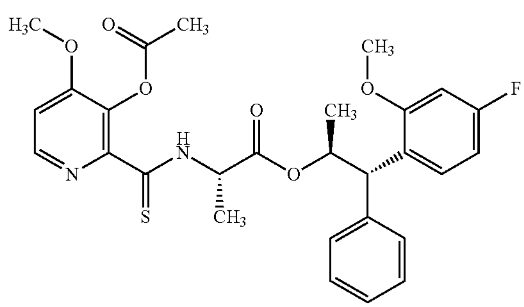 [SMILES: COc1cc(F)ccc1[C@H](c1ccccc1)[C@H](C)OC(=O)[C@H](C)NC(=S)c1nccc(OC)c1OC(C)=O] | WO 2016/109257 Example 1, 2 | Orange Wax |

TABLE 1-continued

Compound Structure, Preparation Method, and Appearance

| Cmpd. No. | Structure | As Prepared According To | Appearance |
|---|---|---|---|
| 45 | 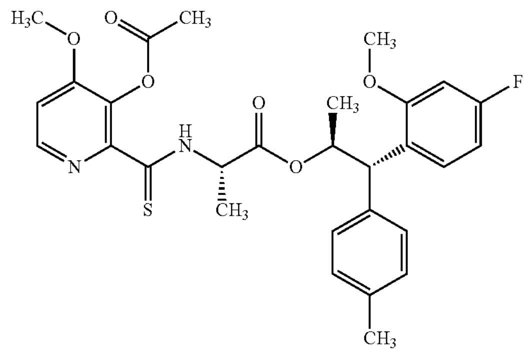 [SMILES: COc1cc(F)ccc1[C@H](c1ccc(C)cc1)[C@H](C)OC(=O)[C@H](C)NC(=S)c1nccc(OC)c1OC(C)=O] | WO 2016/109257 Example 1, 2 | Orange Foam |
| 46 | 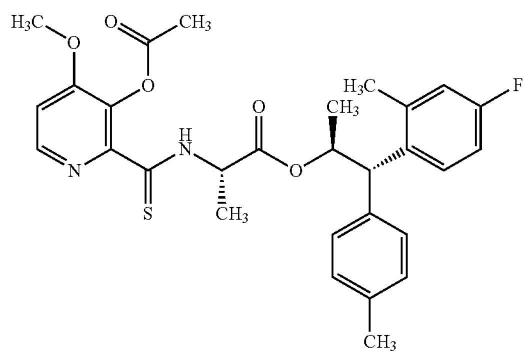 [SMILES: COc1ccnc(C(=S)N[C@@H](C)C(=O)O[C@@H](C)[C@@H](c2ccc(C)cc2)c2ccc(F)cc2C)c1OC(C)=O] | WO 2016/109257 Example 1, 2 | Orange Foam |
| 47 | 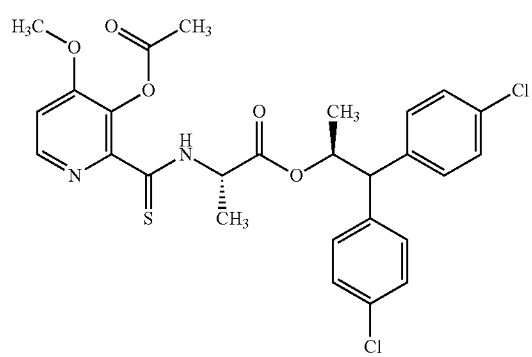 [SMILES: COc1ccnc(C(=S)N[C@@H](C)C(=O)O[C@@H](C)C(c2ccc(Cl)cc2)c2ccc(Cl)cc2)c1OC(C)=O] | WO 2016/109257 Example 1, 2 | Yellow Wax |
| 48 | 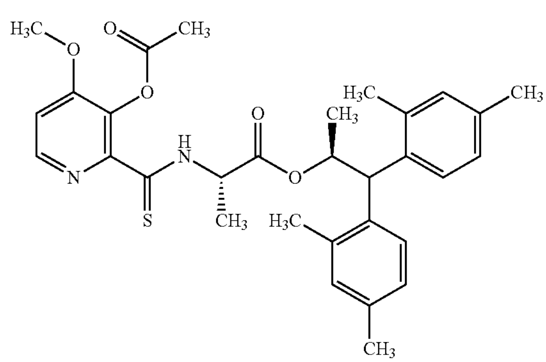 [SMILES: COc1ccnc(C(=S)N[C@@H](C)C(=O)O[C@@H](C)C(c2ccc(C)cc2C)c2ccc(C)cc2C)c1OC(C)=O] | WO 2016/109257 Example 1, 2 | Yellow Wax |

TABLE 1-continued

Compound Structure, Preparation Method, and Appearance

| Cmpd. No. | Structure | As Prepared According To | Appearance |
|---|---|---|---|
| 49 | 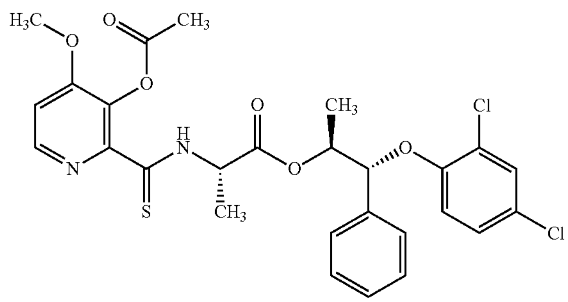 [SMILES: COc1ccnc(C(=S)N[C@@H](C)C(=O)O[C@@H](C)[C@H](Oc2ccc(Cl)cc2Cl)c2ccccc2)c1OC(C)=O] | WO 2016/109304 Example 1, 2 | Orange Foam |
| 50 | 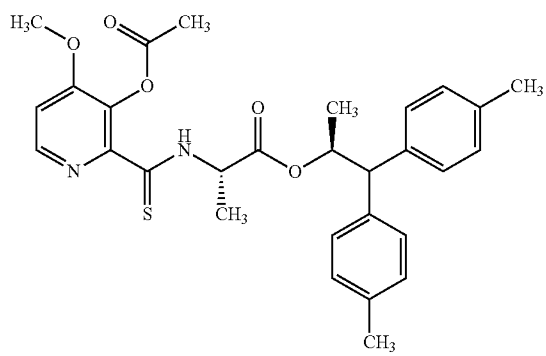 [SMILES: COc1ccnc(C(=S)N[C@@H](C)C(=O)O[C@@H](C)C(c2ccc(C)cc2)c2ccc(C)cc2)c1OC(C)=O] | WO 2016/109257 Example 1, 2 | Orange Foam |
| 51 | 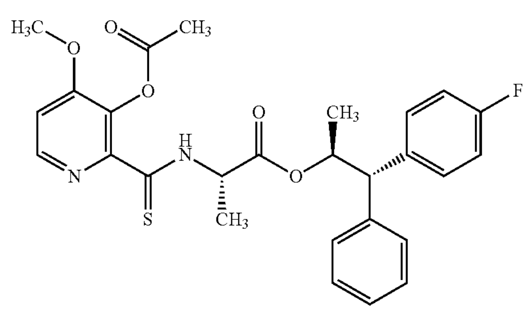 [SMILES: COc1ccnc(C(=S)N[C@@H](C)C(=O)O[C@@H](C)[C@@H](c2ccccc2)c2ccc(F)cc2)c1OC(C)=O] | WO 2016/109257 Example 1, 2 | Red Wax |
| 52 | 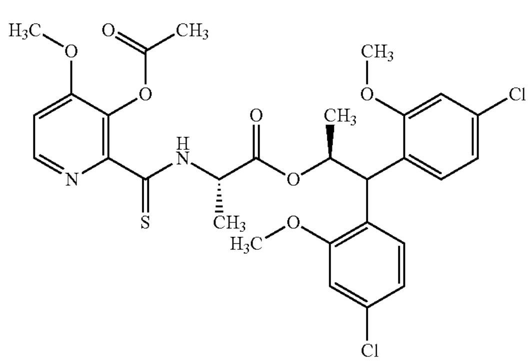 [SMILES: COc1cc(Cl)ccc1C(c1ccc(Cl)cc1OC)[C@H](C)OC(=O)[C@H](C)NC(=S)c1nccc(OC)c1OC(C)=O] | WO 2016/109257 Example 1, 2 | Orange Foam |

TABLE 1-continued

Compound Structure, Preparation Method, and Appearance

| Cmpd. No. | Structure | As Prepared According To | Appearance |
|---|---|---|---|
| 53 | 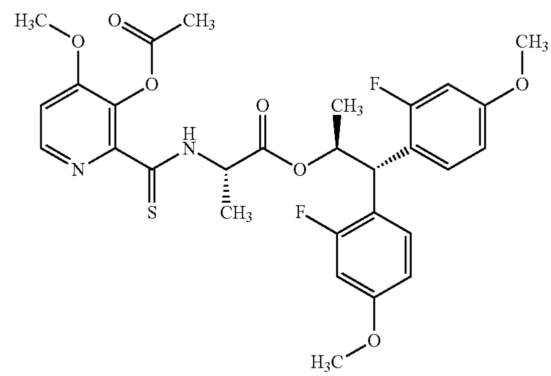 | WO 2016/109257 Example 1, 2 | Orange Foam |
| 54 | 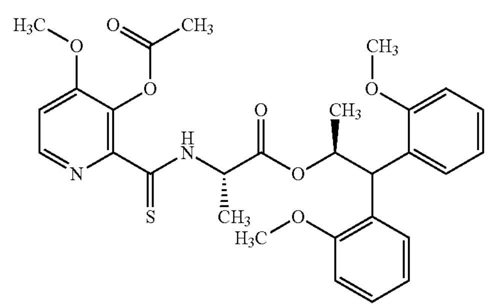 [SMILES: COc1ccccc1C(c1ccccc1OC)[C@H](C)OC(=O)[C@H](C)NC(=S)c1nccc(OC)c1OC(C)=O] | WO 2016/109257 Example 1, 2 | Yellow Foam |
| 55 | 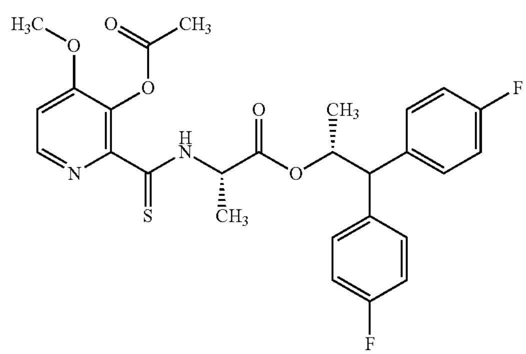 [SMILES: COc1ccnc(C(=S)N[C@@H](C)C(=O)O[C@H](C)C(c2ccc(F)cc2)c2ccc(F)cc2)c1OC(C)=O] | WO 2016/109257 Example 1, 2 | Yellow Foam |
| 56 | 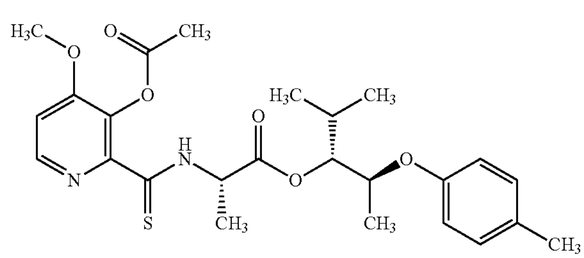 [SMILES: COc1ccnc(C(=S)N[C@@H](C)C(=O)O[C@H](C(C)C)[C@H](C)Oc2ccc(C)cc2)c1OC(C)=O] | WO 2016/109302 Example 1, 2 | Yellow Wax |

TABLE 1-continued

Compound Structure, Preparation Method, and Appearance

| Cmpd. No. | Structure | As Prepared According To | Appearance |
|---|---|---|---|
| 57 | 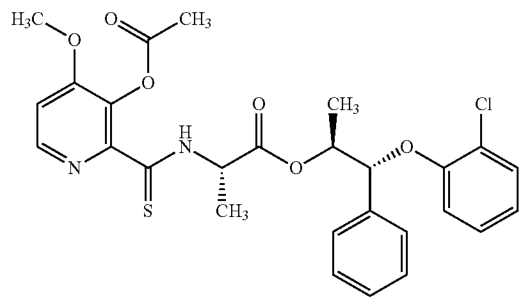 [SMILES: COc1ccnc(C(=S)N[C@@H](C)C(=O)O[C@@H](C)[C@H](Oc2ccccc2Cl)c2ccccc2)c1OC(C)=O] | WO 2016/109304 Example 1, 2 | Yellow Foam |
| 58 | 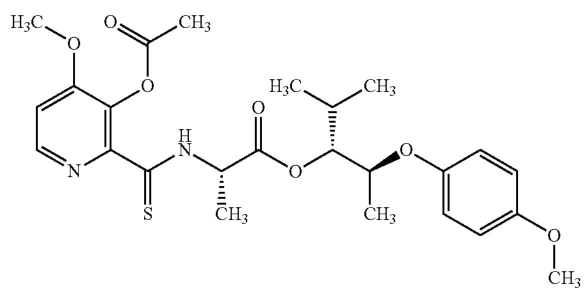 [SMILES: COc1ccc(O[C@@H](C)[C@H](OC(=O)[C@H](C)NC(=S)c2nccc(OC)c2OC(C)=O)C(C)C)cc1] | WO 2016/109302 Example 1, 2 | Yellow Wax |
| 59 | 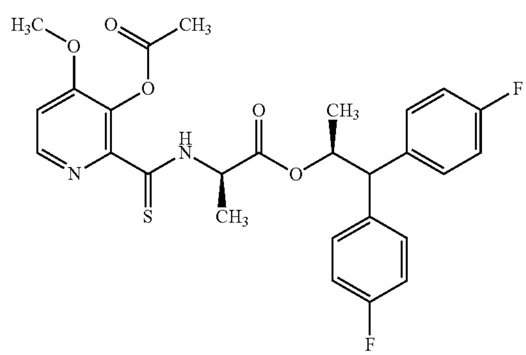 [SMILES: COc1ccnc(C(=S)N[C@H](C)C(=O)O[C@@H](C)C(c2ccc(F)cc2)c2ccc(F)cc2)c1OC(C)=O] | WO 2016/109257 Example 1, 2 | Yellow Foam. |
| 60 | 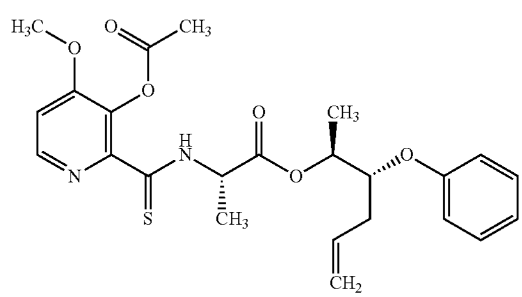 [SMILES: C=CC[C@@H](Oc1ccccc1)[C@H](C)OC(=O)[C@H](C)NC(=S)c1nccc(OC)c1OC(C)=O] | WO 2016/109289 Example 1, 2 | Orange Wax |
| 61 | 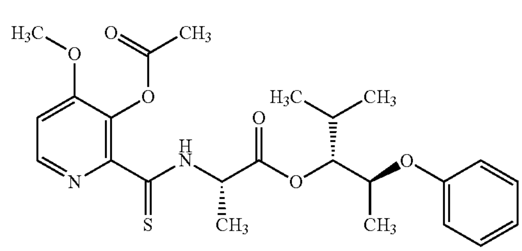 [SMILES: COc1ccnc(C(=S)N[C@@H](C)C(=O)O[C@H](C(C)C)[C@H](C)Oc2ccccc2)c1OC(C)=O] | WO 2016/109302 Example 1, 2 | Orange Wax |

TABLE 1-continued

Compound Structure, Preparation Method, and Appearance

| Cmpd. No. | Structure | As Prepared According To | Appearance |
|---|---|---|---|
| 62 | 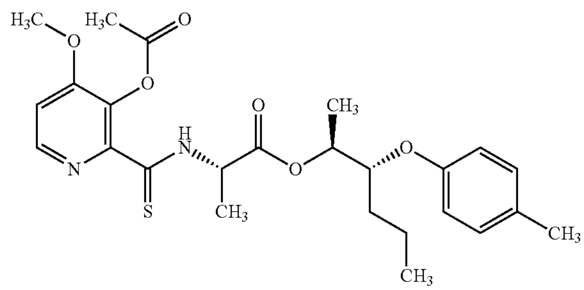 [SMILES: CCC[C@@H](Oc1ccc(C)cc1)[C@H](C)OC(=O)[C@H](C)NC(=S)c1nccc(OC)c1OC(C)=O] | WO 2016/109289 Example 1, 2 | Brown Oil |
| 63 | 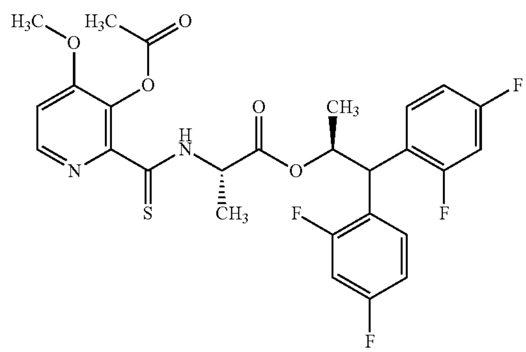 [SMILES: COc1ccnc(C(=S)N[C@@H](C)C(=O)O[C@@H](C)C(c2ccc(F)cc2F)c2ccc(F)cc2F)c1OC(C)=O] | WO 2016/109257 Example 1, 2 | Brown Wax |
| 64 | 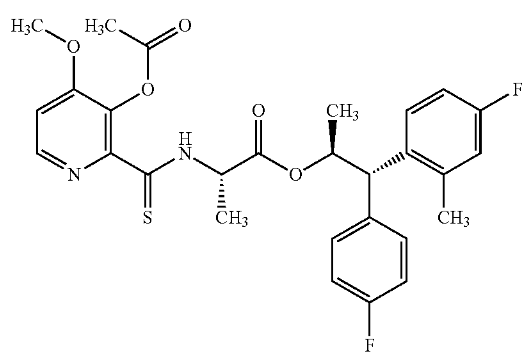 [SMILES: COc1ccnc(C(=S)N[C@@H](C)C(=O)O[C@@H](C)[C@@H](c2ccc(F)cc2)c2ccc(F)cc2C)c1OC(C)=O] | WO 2016/109257 Example 1, 2 | Brown Wax |
| 65 | 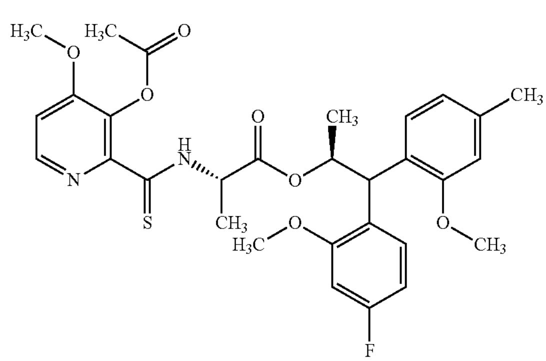 [SMILES: COc1cc(C)ccc1C(c1ccc(F)cc1OC)[C@H](C)OC(=O)[C@H](C)NC(=S)c1nccc(OC)c1OC(C)=O] | WO 2016/109257 Example 1, 2 | Yellow Wax |

TABLE 1-continued

Compound Structure, Preparation Method, and Appearance

| Cmpd. No. | Structure | As Prepared According To | Appearance |
|---|---|---|---|
| 66 | 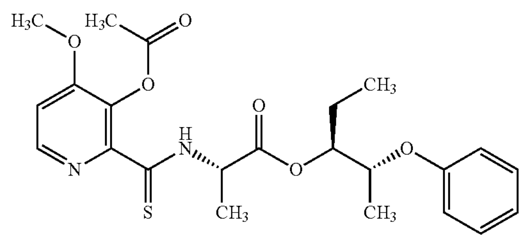 [SMILES: CC[C@H](OC(=O)[C@H](C)NC(=S)c1nccc(OC)c1OC(C)=O)[C@@H](C)Oc1ccccc1] | WO 2016/109302 Example 1, 2 | Brown Oil |
| 67 | 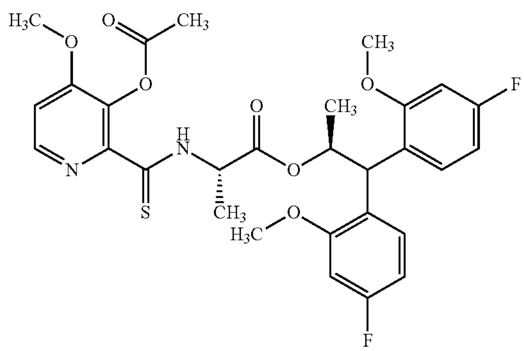 [SMILES: COc1cc(F)ccc1C(c1ccc(F)cc1OC)[C@H](C)OC(=O)[C@H](C)NC(=S)c1nccc(OC)c1OC(C)=O] | WO 2016/109257 Example 1, 2 | Yellow Wax |
| 68 | 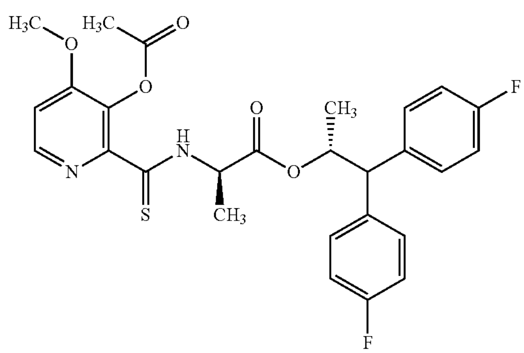 [SMILES: COc1ccnc(C(=S)N[C@H](C)C(=O)O[C@H](C)C(c2ccc(F)cc2)c2ccc(F)cc2)c1OC(C)=O] | WO 2016/109257 Example 1, 2 | Yellow Oil |
| 69 | 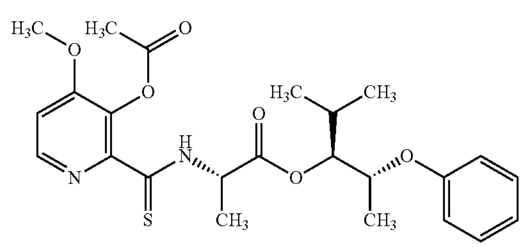 [SMILES: COc1ccnc(C(=S)N[C@@H](C)C(=O)O[C@@H](C(C)C)[C@@H](C)Oc2ccccc2)c1OC(C)=O] | WO 2016/109302 Example 1, 2 | Purple Oil |
| 70 | 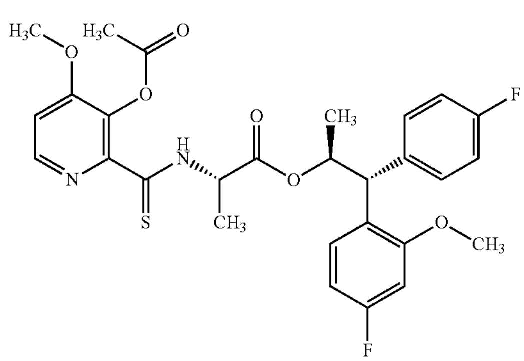 [SMILES: COc1cc(F)ccc1[C@@H](c1ccc(F)cc1)[C@H](C)OC(=O)[C@H](C)NC(=S)c1nccc(OC)c1OC(C)=O] | WO 2016/109257 Example 1, 2 | Brown Wax |

TABLE 1-continued

Compound Structure, Preparation Method, and Appearance

| Cmpd. No. | Structure | As Prepared According To | Appearance |
|---|---|---|---|
| 71 | 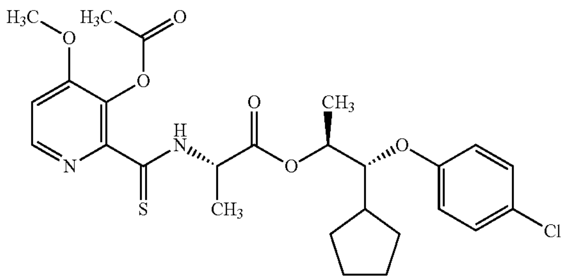 [SMILES: COc1ccnc(C(=S)N[C@@H](C)C(=O)O[C@@H](C)[C@H](Oc2ccc(Cl)cc2)C2CCCC2)c1OC(C)=O] | WO 2016/109289 Example 1, 2 | Yellow Oil |
| 72 | 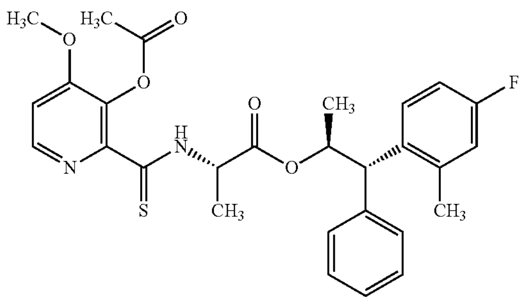 [SMILES: COc1ccnc(C(=S)N[C@@H](C)C(=O)O[C@@H](C)[C@@H](c2ccccc2)c2ccc(F)cc2C)c1OC(C)=O] | WO 2016/109257 Example 1, 2 | Brown Oil |
| 73 | 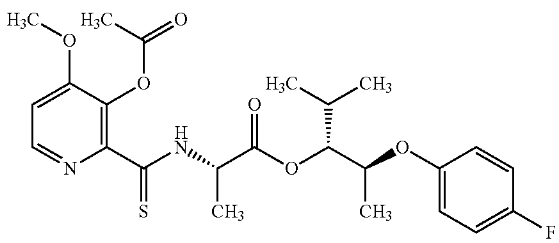 [SMILES: COc1ccnc(C(=S)N[C@@H](C)C(=O)O[C@H](C(C)C)[C@H](C)Oc2ccc(F)cc2)c1OC(C)=O] | WO 2016/109302 Example 1, 2 | Brown Oil |
| 74 | 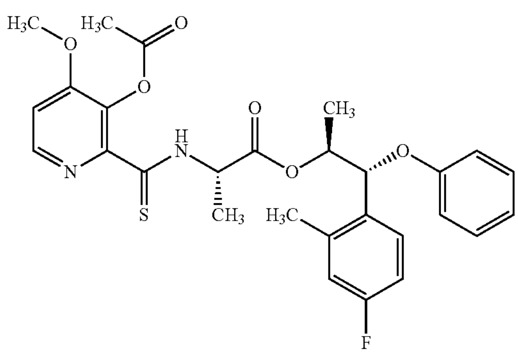 [SMILES: COc1ccnc(C(=S)N[C@@H](C)C(=O)O[C@@H](C)[C@H](Oc2ccccc2)c2ccc(F)cc2C)c1OC(C)=O] | WO 2016/109304 Example 1, 2 | Yellow Wax |
| 75 | 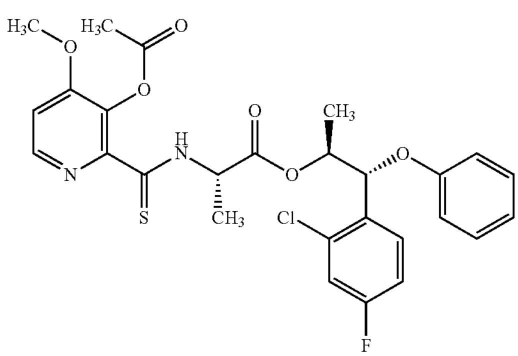 [SMILES: COc1ccnc(C(=S)N[C@@H](C)C(=O)O[C@@H](C)[C@H](Oc2ccccc2)c2ccc(F)cc2Cl)c1OC(C)=O] | WO 2016/109304 Example 1, 2 | Purple Wax |

TABLE 1-continued

Compound Structure, Preparation Method, and Appearance

| Cmpd. No. | Structure | As Prepared According To | Appearance |
|---|---|---|---|
| 76 | (structure) | WO 2016/109302 Example 1, 2 | Brown Oil |
| 77 | (structure) | WO 2016/109289 Example 1, 2 | Brown Wax |
| 78 | (structure) | WO 2016/109257 Example 1, 2 | Yellow Foam |

*Cmpd. No. - Compound Number

TABLE 2

Analytical Data

| Cmpd. No | Melting Point (° C.) | IR (cm$^{-1}$) | MASS SPEC | NMR |
|---|---|---|---|---|
| 1 | | IR (thin film) 3095, 2963, 1752, 1510, 1480, 1245, 1231, 796 cm$^{-1}$ | | $^1$H NMR (400 MHz, CDCl$_3$) δ 12.92 (s, 1H), 10.75 (s, 1H), 7.97 (s, 1H), 7.06 (d, J = 8.4 Hz, 2H), 6.87 (s, 1H), 6.78 (d, J = 8.6 Hz, 2H), 5.18 (p, J = 7.2 Hz, 1H), 5.08 (t, J = 5.7 Hz, 1H), 4.47 (p, J = 6.2 Hz, 1H), 3.96 (s, 3H), 2.27 (s, 3H), 2.14 (pd, J = 6.9, 5.1 Hz, 1H), 1.70 (d, J = 7.1 Hz, 3H), 1.30 (d, J = 6.2 Hz, 3H), 0.97 (d, J = 6.9 Hz, 3H), 0.93 (d, J = 6.7 Hz, 3H). |
| 2 | | IR (thin film) 2935, 1733, 1512, 1487, 1453, 1272, 1202, 1089, 796 cm$^{-1}$ | HRMS-ESI (m/z) [M + H]$^+$ calcd for C$_{25}$H$_{25}$Cl$_2$N$_2$O$_4$S, 519.0907; found, 519.0937 | $^1$H NMR (400 MHz, CDCl$_3$) δ 12.84 (s, 1H), 10.62 (s, 1H), 7.90 (s, 1H), 7.28-7.23 (m, 4H), 7.19-7.15 (m, 4H), 6.85 (d, J = 5.3 Hz, 1H), 5.79-5.70 (m, 1H), 4.91 (p, J = 7.2 Hz, 1H), 4.04 (d, J = 9.7 Hz, 1H), 3.97 (s, 3H), 1.26 (d, J = 6.1 Hz, 3H), 1.17 (d, J = 7.2 Hz, 3H). |
| 3 | | IR (thin film) 2935, 1733, 1712, | HRMS-ESI (m/z) [M + H]$^+$ calcd for C$_{29}$H$_{35}$N$_2$O$_4$S, | $^1$H NMR (400 MHz, CDCl$_3$) δ 12.87 (s, 1H), 10.83 (s, 1H), 7.91 (s, 1H), 7.19 (d, J = 7.9 Hz, 1H), 7.12 (d, J = |

TABLE 2-continued

Analytical Data

| Cmpd. No | Melting Point (° C.) | IR (cm$^{-1}$) | MASS SPEC | NMR |
|---|---|---|---|---|
|  |  | 1514, 1283, 1206, 735 cm$^{-1}$ | 507.2312; found, 507.2341 | 7.7 Hz, 1H), 7.00-6.89 (m, 3H), 6.89-6.82 (m, 2H), 5.71 (dq, J = 10.0, 6.1 Hz, 1H), 4.88 (p, J = 7.2 Hz, 1H), 4.46 (d, J = 10.1 Hz, 1H), 3.96 (s, 3H), 2.36 (s, 3H), 2.30 (s, 3H), 2.25 (s, 3H), 2.22 (s, 3H), 1.32 (d, J = 6.1 Hz, 3H), 1.12 (d, J = 7.2 Hz, 3H). |
| 4 |  | IR (thin film) 1733, 1509, 1486, 1207, 735 cm$^{-1}$ | HRMS-ESI (m/z) [M + H]$^+$ calcd for C$_{25}$H$_{26}$FN$_2$O$_4$S, 469.1592; found, 469.1618 | $^1$H NMR (400 MHz, CDCl$_3$) δ 11.05 (s, 1H), 7.99 (s, 1H), 7.33-7.19 (m, 6H), 7.15 (t, J = 7.1 Hz, 1H), 6.96 (t, J = 8.6 Hz, 3H), 5.78 (dq, J = 12.1, 6.2 Hz, 1H), 4.85 (s, 1H), 4.06 (d, J = 10.0 Hz, 1H), 3.99 (s, 3H), 1.26 (d, J = 6.1 Hz, 3H), 1.04 (d, J = 7.1 Hz, 3H). |
| 5 |  | IR (thin film) 2936, 1734, 1622, 1506, 1283, 1154, 1030 cm$^{-1}$ | HRMS-ESI (m/z) [M + H]$^+$ calcd for C$_{27}$H$_{29}$F$_2$N$_2$O$_6$S, 547.1709; found, 547.1743 | $^1$H NMR (400 MHz, CDCl$_3$) δ 12.89 (s, 1H), 10.58 (s, 1H), 7.93 (s, 1H), 7.31-7.26 (m, 1H), 7.21-7.13 (m, 1H), 6.86 (d, J = 5.2 Hz, 1H), 6.64-6.56 (m, 3H), 6.49 (dd, J = 12.1, 2.6 Hz, 1H), 5.81 (dq, J = 12.3, 6.3 Hz, 1H), 4.94 (p, J = 7.2 Hz, 1H), 4.63 (d, J = 10.2 Hz, 1H), 3.96 (s, 3H), 3.76 (s, 3H), 3.73 (s, 3H), 1.30 (d, J = 6.1 Hz, 3H), 1.21 (d, J = 7.2 Hz, 3H). |
| 6 |  | IR (thin film) 2933, 1732, 1511, 1485, 1276, 1203, 1157, 797 cm$^{-1}$ | HRMS-ESI (m/z) [M + H]$^+$ calcd for C$_{27}$H$_{30}$FN$_2$O$_4$S, 498.1936; found, 498.1969 | $^1$H NMR (400 MHz, CDCl$_3$) δ 12.88 (s, 1H), 10.60 (s, 1H), 7.91 (s, 1H), 7.29 (dd, J = 8.6, 5.8 Hz, 1H), 7.16-7.11 (m, 2H), 7.04-6.99 (m, 2H), 6.92-6.81 (m, 3H), 5.78 (dq, J = 10.1, 6.1 Hz, 1H), 4.89 (p, J = 7.2 Hz, 1H), 4.26 (d, J = 10.3 Hz, 1H), 3.96 (s, 3H), 2.38 (s, 3H), 2.25 (s, 3H), 1.28 (d, J = 6.1 Hz, 3H), 1.10 (d, J = 7.2 Hz, 3H). |
| 7 |  | IR (thin film) 2981, 1732, 1507, 1485, 1221, 729 cm$^{-1}$ | HRMS-ESI (m/z) [M + H]$^+$ calcd for C$_{25}$H$_{25}$F$_2$N$_2$O$_4$S, 487.1498; found, 487.1526 | $^1$H NMR (400 MHz, CDCl$_3$) δ 12.88 (s, 1H), 10.43 (d, J = 7.7 Hz, 1H), 7.98 (dd, J = 5.1, 1.6 Hz, 1H), 7.21 (ddd, J = 13.5, 8.6, 5.3 Hz, 4H), 7.06-6.87 (m, 5H), 5.70 (dq, J = 9.0, 6.1 Hz, 1H), 5.00-4.83 (m, 1H), 4.06 (d, J = 9.1 Hz, 1H), 3.96 (d, J = 1.6 Hz, 3H), 1.43 (d, J = 7.1 Hz, 3H), 1.23 (d, J = 6.1 Hz, 3H). |
| 8 |  | IR (thin film) 3089, 2934, 1753, 1494, 1481, 1228, 793 cm$^{-1}$ |  | $^1$H NMR (400 MHz, CDCl$_3$) δ 12.92 (s, 1H), 10.69 (s, 1H), 7.97 (s, 1H), 7.32-7.21 (m, 2H), 6.98-6.91 (m, 1H), 6.91-6.83 (m, 3H), 5.25-4.92 (m, 2H), 4.49 (qd, J = 6.3, 4.3 Hz, 1H), 3.96 (s, 3H), 1.80-1.67 (m, 2H), 1.64 (d, J = 7.1 Hz, 3H), 1.40-1.23 (m, 9H), 0.91-0.82 (m, 3H). |
| 9 |  | IR (thin film) 2938, 1738, 1513, 1478, 1283, 1247, 1202, 733 cm$^{-1}$ | HRMS-ESI (m/z) [M + H]$^+$ calcd for C$_{25}$H$_{25}$Cl$_2$N$_2$O$_5$S, 535.0856; found, 535.0883 | $^1$H NMR (400 MHz, CDCl$_3$) δ 12.80 (s, 1H), 10.58 (d, J = 7.5 Hz, 1H), 7.94 (d, J = 5.1 Hz, 1H), 7.39-7.27 (m, 6H), 6.94 (dd, J = 8.9, 2.6 Hz, 1H), 6.86 (d, J = 5.1 Hz, 1H), 6.54 (d, J = 8.8 Hz, 1H), 5.36 (qd, J = 6.5, 4.5 Hz, 1H), 5.25 (d, J = 4.5 Hz, 1H), 5.01 (p, J = 7.2 Hz, 1H), 3.96 (s, 3H), 1.46 (d, J = 7.2 Hz, 3H), 1.43 (d, J = 6.5 Hz, 3H). |
| 10 |  | IR (thin film) 2930, 2858, 1738, 1511, 1486, 1199, 728 cm$^{-1}$ | HRMS-ESI (m/z) [M + H]$^+$ calcd for C$_{24}$H$_{33}$N$_2$O$_5$S, 461.2105; found, 461.2206 | $^1$H NMR (400 MHz, CDCl$_3$) δ 12.89 (s, 1H), 10.78 (s, 1H), 7.90 (s, 1H), 7.30-7.20 (m, 2H), 6.99-6.90 (m, 1H), 6.89-6.81 (m, 3H), 5.20 (dt, J = 9.0, 4.0 Hz, 1H), 5.10 (p, J = 7.2 Hz, 1H), 4.47 (qd, J = 6.3, 3.8 Hz, 1H), 3.96 (s, 3H), 1.81-1.65 (m, 2H), 1.63 (d, J = 7.2 Hz, 3H), 1.49-1.36 (m, 1H), 1.33 (d, J = 6.3 Hz, 3H), 1.32-1.24 (m, 5H), 0.93-0.84 (m, 3H). |

TABLE 2-continued

Analytical Data

| Cmpd. No | Melting Point (° C.) | IR (cm$^{-1}$) | MASS SPEC | NMR |
|---|---|---|---|---|
| 11 | | IR (thin film) 3092, 2966, 1752, 1505, 1473, 1229, 1195, 797 cm$^{-1}$ | HRMS-ESI (m/z) [M + H]$^+$ calcd for C$_{23}$H$_{31}$N$_2$O$_6$S, 463.1897; found, 463.1923 | $^1$H NMR (400 MHz, CDCl$_3$) δ 12.93 (s, 1H), 10.76 (d, J = 7.6 Hz, 1H), 7.98 (dd, J = 5.0, 1.0 Hz, 1H), 6.88 (d, J = 5.1 Hz, 1H), 6.82 (d, J = 1.3 Hz, 4H), 5.18 (p, J = 7.2 Hz, 1H), 5.07 (t, J = 5.7 Hz, 1H), 4.39 (p, J = 6.1 Hz, 1H), 3.95 (d, J = 1.0 Hz, 3H), 3.76 (d, J = 0.8 Hz, 3H), 2.19-2.09 (m, 1H), 1.70 (d, J = 7.1 Hz, 3H), 1.29 (d, J = 6.2 Hz, 3H), 0.97 (d, J = 6.9 Hz, 3H), 0.95 (d, J = 6.8 Hz, 3H). |
| 12 | | IR (thin film) 2935, 1733, 1501, 1512, 1277, 1204, 698 cm$^{-1}$ | HRMS-ESI (m/z) [M + H]$^+$ calcd for C$_{26}$H$_{28}$FN$_2$O$_5$S, 499.1697; found, 499.1722 | $^1$H NMR (400 MHz, CDCl$_3$) δ 12.89 (s, 1H), 10.57 (d, J = 7.6 Hz, 1H), 8.03-7.84 (m, 1H), 7.37-7.29 (m, 2H), 7.26-7.11 (m, 4H), 6.86 (d, J = 5.3 Hz, 1H), 6.62-6.54 (m, 2H), 5.88 (dq, J = 10.0, 6.2 Hz, 1H), 4.89 (p, J = 7.2 Hz, 1H), 4.56 (d, J = 10.1 Hz, 1H), 3.94 (s, 3H), 3.84 (s, 3H), 1.27 (d, J = 6.1 Hz, 3H), 1.04 (d, J = 7.2 Hz, 3H). |
| 13 | | IR (thin film) 2933, 2835, 1731, 1512, 1489, 1243, 1204, 751 cm$^{-1}$ | HRMS-ESI (m/z) [M + H]$^+$ calcd for C$_{27}$H$_{31}$N$_2$O$_6$S, 511.1897; found, 511.1961 | $^1$H NMR (400 MHz, CDCl$_3$) δ 12.92 (s, 1H), 10.61 (d, J = 7.6 Hz, 1H), 7.96 (d, J = 5.2 Hz, 1H), 7.47 (dd, J = 7.6, 1.7 Hz, 1H), 7.26 (dd, J = 7.8, 1.8 Hz, 1H), 7.17-7.08 (m, 2H), 6.91-6.81 (m, 4H), 6.77 (dd, J = 8.2, 1.1 Hz, 1H), 6.01 (dq, J = 10.0, 6.2 Hz, 1H), 5.02 (d, J = 10.0 Hz, 1H), 4.96-4.84 (m, 1H), 3.93 (s, 3H), 3.85 (s, 3H), 3.76 (s, 3H), 1.27 (d, J = 6.1 Hz, 3H), 1.07 (d, J = 7.1 Hz, 3H). |
| 14 | | IR (thin film) 2938, 1734, 1514, 1489, 1248, 733 cm$^{-1}$ | HRMS-ESI (m/z) [M + H]$^+$ calcd for C$_{27}$H$_{29}$Cl$_2$N$_2$O$_6$S, 579.1118; found, 579.1142 | $^1$H NMR (400 MHz, CDCl$_3$) δ 12.88 (s, 1H), 10.56 (d, J = 7.6 Hz, 1H), 8.01-7.88 (m, 1H), 7.33 (d, J = 8.3 Hz, 1H), 7.15-7.08 (m, 1H), 6.89-6.73 (m, 5H), 5.92 (dq, J = 9.8, 6.2 Hz, 1H), 4.97-4.86 (m, 1H), 4.84 (d, J = 9.7 Hz, 1H), 3.94 (s, 3H), 3.83 (s, 3H), 3.74 (s, 3H), 1.25 (d, J = 6.3 Hz, 3H), 1.17 (d, J = 7.1 Hz, 3H). |
| 15 | | IR (thin film) 2980, 1732, 1506, 1220, 727 cm$^{-1}$ | HRMS-ESI (m/z) [M + H]$^+$ calcd for C$_{25}$H$_{25}$F$_2$N$_2$O$_4$S, 487.1498; found, 487.1531 | $^1$H NMR (400 MHz, CDCl$_3$) δ 12.88 (s, 1H), 10.44 (s, 1H), 7.93 (s, 1H), 7.25-7.15 (m, 4H), 6.94 (dq, J = 23.7, 7.5, 6.4 Hz, 5H), 5.70 (dq, J = 8.9, 6.2 Hz, 1H), 4.91 (p, J = 7.2 Hz, 1H), 4.06 (d, J = 8.9 Hz, 1H), 3.98 (s, 3H), 1.41 (d, J = 7.2 Hz, 3H), 1.22 (d, J = 6.2 Hz, 3H). |
| 16 | | IR (thin film) 3092, 2990, 1749, 1512, 1479, 1228, 1209, 798 cm$^{-1}$ | HRMS-ESI (m/z) [M + Na]$^+$ calcd for C$_{22}$H$_{26}$N$_2$NaO$_5$S, 453.1455; found, 453.1504 | $^1$H NMR (400 MHz, CDCl$_3$) δ 12.89 (d, J = 0.6 Hz, 1H), 10.65 (d, J = 7.7 Hz, 1H), 7.95 (d, J = 5.1 Hz, 1H), 7.27-7.20 (m, 2H), 6.98-6.85 (m, 4H), 5.96-5.80 (m, 1H), 5.24-5.18 (m, 1H), 5.18-5.08 (m, 2H), 5.08-4.99 (m, 1H), 4.49-4.39 (m, 1H), 3.95 (s, 3H), 2.55-2.36 (m, 2H), 1.50 (d, J = 7.1 Hz, 3H), 1.40 (d, J = 6.5 Hz, 3H). |
| 17 | | IR (thin film) 3091, 2964, 1746, 1511, 1280, 1200, 980 cm$^{-1}$ | HRMS-ESI (m/z) [M + H]$^+$ calcd for C$_{22}$H$_{28}$ClN$_2$O$_5$S, 467.1402; found, 467.1432 | $^1$H NMR (400 MHz, CDCl$_3$) δ 12.86 (s, 1H), 10.55 (d, J = 7.5 Hz, 1H), 7.93 (dd, J = 5.1, 1.6 Hz, 1H), 7.10 (d, J = 8.7 Hz, 2H), 6.87 (d, J = 5.4 Hz, 1H), 6.86-6.77 (m, 2H), 5.25 (qd, J = 6.5, 3.6 Hz, 1H), 5.01-4.91 (m, 1H), 4.14 (dd, J = 7.3, 3.7 Hz, 1H), 3.96 (d, J = 1.6 Hz, 3H), 1.95 (h, J = 6.8 Hz, 1H), 1.39 (d, J = 7.2 Hz, 3H), 1.35 (t, J = 6.4 Hz, 3H), 1.00 (d, J = 6.8 Hz, 6H). |
| 18 | | IR (thin film) 2935, 1732, 1513, 1501, 1278, 1204 cm$^{-1}$ | HRMS-ESI (m/z) [M + H]$^+$ calcd for C$_{27}$H$_{30}$FN$_2$O$_5$S, 513.1854; found, 513.1881 | $^1$H NMR (400 MHz, CDCl$_3$) δ 12.90 (s, 1H), 10.57 (d, J = 7.6 Hz, 1H), 7.97 (d, J = 5.1 Hz, 1H), 7.25-7.18 (m, 2H), 7.18-7.10 (m, 1H), 7.06-6.98 (m, 2H), 6.87 (d, J = 5.2 Hz, 1H), 6.60-6.52 (m, 2H), 5.85 (dq, J = 9.8, 6.2 Hz, 1H), 4.90 (p, J = 7.1 Hz, 1H), 4.53 |

TABLE 2-continued

Analytical Data

| Cmpd. No | Melting Point (° C.) | IR (cm$^{-1}$) | MASS SPEC | NMR |
|---|---|---|---|---|
| 19 | | IR (thin film) 3094, 2970, 1752, 1512, 1480, 1247, 1230, 795 cm$^{-1}$ | HRMS-ESI (m/z) [M + Na]$^+$ calcd for C$_{22}$H$_{28}$N$_2$NaO$_5$S, 455.1611; found, 455.163 | (d, J = 9.9 Hz, 1H), 3.94 (s, 3H), 3.83 (s, 3H), 2.26 (s, 3H), 1.26 (d, J = 6.2 Hz, 3H), 1.08 (d, J = 7.1 Hz, 3H). $^1$H NMR (400 MHz, CDCl$_3$) δ 12.92 (s, 1H), 10.75 (s, 1H), 7.97 (d, J = 5.1 Hz, 1H), 7.29-7.24 (m, 2H), 6.98-6.91 (m, 1H), 6.91-6.85 (m, 3H), 5.18 (p, J = 7.2 Hz, 1H), 5.10 (t, J = 5.7 Hz, 1H), 4.53 (p, J = 6.2 Hz, 1H), 3.96 (s, 3H), 2.23-2.06 (m, 1H), 1.70 (d, J = 7.2 Hz, 3H), 1.32 (d, J = 6.1 Hz, 3H), 0.98 (d, J = 6.9 Hz, 3H), 0.93 (d, J = 6.8 Hz, 3H). |
| 20 | | IR (thin film) 2979, 1732, 1511, 1485, 1278, 1204, 730 cm$^{-1}$ | HRMS-ESI (m/z) [M + H]$^+$ calcd for C$_{27}$H$_{31}$N$_2$O$_4$S, 479.1999; found, 479.2023 | $^1$H NMR (400 MHz, CDCl$_3$) δ 12.90 (s, 1H), 10.57 (s, 1H), 7.96 (s, 1H), 7.20-7.14 (m, 4H), 7.07 (d, J = 7.9 Hz, 2H), 7.03 (d, J = 7.9 Hz, 2H), 6.85 (s, 1H), 5.80 (dq, J = 10.1, 6.1 Hz, 1H), 4.96-4.83 (m, 1H), 3.99 (d, J = 10.1 Hz, 1H), 3.94 (s, 3H), 2.27 (s, 3H), 2.24 (s, 3H), 1.27 (d, J = 6.1 Hz, 3H), 1.07 (d, J = 7.2 Hz, 3H). |
| 21 | | IR (thin film) 2956, 1737, 1512, 1485, 1280, 1201, 729 cm$^{-1}$ | HRMS-ESI (m/z) [M + H]$^+$ calcd for C$_{23}$H$_{32}$N$_2$O$_5$S, 447.1948; found, 447.2048 | $^1$H NMR (400 MHz, CDCl$_3$) δ 12.90 (s, 1H), 10.70 (s, 1H), 7.96 (s, 1H), 7.31-7.18 (m, 2H), 6.98-6.89 (m, 1H), 6.88-6.83 (m, 3H), 5.30 (d, J = 8.9 Hz, 1H), 5.09 (p, J = 7.1 Hz, 1H), 4.46 (qd, J = 6.4, 3.5 Hz, 1H), 3.95 (s, 3H), 1.74 (dddt, J = 17.9, 8.8, 6.4, 3.3 Hz, 2H), 1.61 (d, J = 7.2 Hz, 3H), 1.42 (ddd, J = 13.7, 8.9, 2.9 Hz, 1H), 1.32 (d, J = 6.3 Hz, 3H), 0.96 (d, J = 6.5 Hz, 3H), 0.94 (d, J = 6.5 Hz, 3H). |
| 22 | | IR (thin film) 2937, 1735, 1512, 1481, 1274, 1245, 1201, 1059, 728 cm$^{-1}$ | HRMS-ESI (m/z) [M + H]$^+$ calcd for C$_{25}$H$_{26}$ClN$_2$O$_5$S, 501.1245; found, 501.1272 | $^1$H NMR (400 MHz, CDCl$_3$) δ 12.83 (s, 1H), 10.62 (d, J = 7.5 Hz, 1H), 7.95 (d, J = 5.1 Hz, 1H), 7.45-7.38 (m, 2H), 7.37-7.28 (m, 4H), 6.99 (ddd, J = 8.3, 7.5, 1.7 Hz, 1H), 6.86 (d, J = 5.1 Hz, 1H), 6.81 (td, J = 7.7, 1.4 Hz, 1H), 6.65 (dd, J = 8.4, 1.5 Hz, 1H), 5.42-5.35 (m, 1H), 5.29 (d, J = 4.8 Hz, 1H), 5.03 (p, J = 7.2 Hz, 1H), 3.95 (d, J = 2.8 Hz, 3H), 1.46 (d, J = 6.4 Hz, 3H), 1.42 (d, J = 7.2 Hz, 3H). |
| 23 | 59-75 | IR (thin film) 2938, 1734, 1600, 1515, 1501, 1454, 1278, 955, 733 cm$^{-1}$ | HRMS-ESI (m/z) [M + Na]$^+$ calcd for C$_{27}$H$_{28}$F$_2$N$_2$O$_6$SNa, 569.1528; found, 569.1542 | $^1$H NMR (500 MHz, CDCl$_3$) δ 12.89 (s, 1H), 10.58 (s, 1H), 7.97 (d, J = 5.2 Hz, 1H), 7.37 (dd, J = 8.5, 6.7 Hz, 1H), 7.14 (dd, J = 8.4, 6.7 Hz, 1H), 6.90-6.79 (m, 1H), 6.60-6.45 (m, 4H), 6.00-5.86 (m, 1H), 4.95-4.87 (m, 1H), 4.83 (d, J = 9.7 Hz, 1H), 3.96 (s, 3H), 3.83 (s, 3H), 3.74 (s, 3H), 1.24 (d, J = 6.2 Hz, 3H), 1.18-1.13 (m, 3H). |
| 24 | 54-70 | IR (thin film) 2938, 1735, 1601, 1510, 1455, 1281, 1206, 733 cm$^{-1}$ | HRMS-ESI (m/z) [M + Na]$^+$ calcd for C$_{26}$H$_{26}$F$_2$N$_2$O$_5$SNa, 539.1423; found, 539.1431 | $^1$H NMR (500 MHz, CDCl$_3$) δ 12.87 (s, 1H), 10.56 (d, J = 7.7 Hz, 1H), 7.97 (d, J = 5.1 Hz, 1H), 7.29-7.19 (m, 3H), 6.95 (t, J = 8.7 Hz, 2H), 6.87 (d, J = 5.1 Hz, 1H), 6.59 (td, J = 8.3, 2.5 Hz, 1H), 6.53 (dd, J = 10.8, 2.5 Hz, 1H), 5.80 (dq, J = 10.0, 6.2 Hz, 1H), 4.98-4.86 (m, 1H), 4.51 (d, J = 10.1 Hz, 1H), 3.95 (s, 3H), 3.77 (s, 3H), 1.24 (d, J = 6.2 Hz, 3H), 1.14 (d, J = 7.1 Hz, 3H). |
| 25 | 80-86 | IR (thin film) 2973, 2938, 1742, 1514, 1488, 1285, 1246, 1204, 738 cm$^{-1}$ | HRMS-ESI (m/z) [M + Na]$^+$ calcd for C$_{21}$H$_{26}$N$_2$O$_5$SNa, 441.1455; found, 441.1453 | $^1$H NMR (500 MHz, CDCl$_3$) δ 12.90 (s, 1H), 10.74 (s, 1H), 7.92 (s, 1H), 7.49-7.15 (m, 2H), 6.93 (tt, J = 7.3, 1.1 Hz, 1H), 6.90-6.79 (m, 3H), 5.19-5.04 (m, 2H), 4.48 (qd, J = 6.3, 4.1 Hz, 1H), 3.96 (s, 3H), 1.83-1.71 (m, 2H), 1.64 (d, J = 7.1 Hz, 3H), 1.33 (d, J = 6.4 Hz, 3H), 0.98 (t, J = 7.5 Hz, 3H). |

TABLE 2-continued

Analytical Data

| Cmpd. No | Melting Point (° C.) | IR (cm$^{-1}$) | MASS SPEC | NMR |
|---|---|---|---|---|
| 26 | 152-159 | IR (thin film) 2982, 1736, 1515, 1495, 1454, 1278, 1206, 736 cm$^{-1}$ | HRMS-ESI (m/z) [M + Na]$^+$ calcd for C$_{26}$H$_{27}$FN$_2$O$_4$SNa, 505.1568; found, 505.1581 | $^1$H NMR (500 MHz, CDCl$_3$) δ 12.88 (s, 1H), 10.57 (s, 1H), 7.93 (s, 1H), 7.31 (dd, J = 8.7, 5.8 Hz, 1H), 7.28-7.25 (m, 2H), 7.24-7.19 (m, 2H), 7.17-7.09 (m, 1H), 6.89 (td, J = 8.3, 2.8 Hz, 1H), 6.87-6.83 (m, 2H), 5.80 (dq, J = 10.4, 6.2 Hz, 1H), 4.94-4.82 (m, 1H), 4.31 (d, J = 10.4 Hz, 1H), 3.96 (s, 3H), 2.39 (s, 3H), 1.30 (d, J = 6.1 Hz, 3H), 1.06 (d, J = 7.1 Hz, 3H). |
| 27 | 46-63 | IR (thin film) 2966, 1742, 1513, 1489, 1456, 1283, 1244, 1202, 734 cm$^{-1}$ | HRMS-ESI (m/z) [M + Na]$^+$ calcd for C$_{22}$H$_{28}$N$_2$O$_5$SNa, 455.1611; found, 455.1620 | $^1$H NMR (500 MHz, CDCl$_3$) δ 12.92 (s, 1H), 10.77 (s, 1H), 7.94 (s, 1H), 7.30-7.23 (m, 2H), 6.94 (tt, J = 7.3, 1.0 Hz, 1H), 6.89-6.81 (m, 3H), 5.23-5.13 (m, 1H), 5.10 (dd, J = 7.0, 4.9 Hz, 1H), 4.55 (qd, J = 6.2, 4.8 Hz, 1H), 3.96 (s, 3H), 2.06 (h, J = 6.9 Hz, 1H), 1.72 (d, J = 7.2 Hz, 3H), 1.33 (d, J = 6.2 Hz, 3H), 1.00 (d, J = 6.9 Hz, 3H), 0.97 (d, J = 6.7 Hz, 3H). |
| 28 | 53-64 | | HRMS-ESI (m/z) [M + Na]$^+$ calcd for C$_{25}$H$_{24}$F$_2$N$_2$O$_4$SNa, 509.1317; found, 509.1330 | $^1$H NMR (500 MHz, CDCl$_3$) δ 12.84 (s, 1H), 10.60 (s, 1H), 7.91 (s, 1H), 7.26-7.19 (m, 4H), 6.98 (t, J = 8.6 Hz, 2H), 6.93 (t, J = 8.6 Hz, 2H), 6.86 (d, J = 5.2 Hz, 1H), 5.74 (dq, J = 9.6, 6.1 Hz, 1H), 4.95-4.86 (m, 1H), 4.06 (d, J = 9.8 Hz, 1H), 3.97 (s, 3H), 1.26 (d, J = 6.1 Hz, 3H), 1.14 (d, J = 7.1 Hz, 3H).<br>$^{19}$F NMR (471 MHz, CDCl$_3$) δ −115.46, −115.84. |
| 29 | 60-72 | IR (thin film) 2935, 1734, 1514, 1456, 1271, 1207, 1041, 734 cm$^{-1}$ | HRMS-ESI (m/z) [M + Na]$^+$ calcd for C$_{29}$H$_{34}$N$_2$O$_6$SNa, 561.2030; found, 561.2027 | $^1$H NMR (500 MHz, CDCl$_3$) δ 12.94 (s, 1H), 10.65 (s, 1H), 7.93 (s, 1H), 7.31 (d, J = 7.8 Hz, 1H), 7.11 (d, J = 8.1 Hz, 1H), 6.85 (d, J = 5.2 Hz, 1H), 6.68-6.62 (m, 3H), 6.57 (d, J = 1.6 Hz, 1H), 5.95 (dq, J = 9.9, 6.2 Hz, 1H), 4.95-4.87 (m, 2H), 3.95 (s, 3H), 3.83 (s, 3H), 3.74 (s, 3H), 2.27 (s, 3H), 2.25 (s, 3H), 1.25 (d, J = 6.2 Hz, 3H), 1.09 (d, J = 7.1 Hz, 3H). |
| 30 | 50-60 | IR (thin film) 2938, 1739, 1513, 1488, 1272, 1226, 1202, 907, 731 cm$^{-1}$ | HRMS-ESI (m/z) [M + Na]$^+$ calcd for C$_{25}$H$_{24}$ClFN$_2$O$_5$SNa, 541.0971; found, 541.0979 | $^1$H NMR (500 MHz, CDCl$_3$) δ 12.85 (s, 1H), 10.61 (s, 1H), 7.90 (s, 1H), 7.46 (dd, J = 8.8, 6.0 Hz, 1H), 7.21-7.15 (m, 2H), 7.09 (dd, J = 8.3, 2.6 Hz, 1H), 6.94-6.86 (m, 2H), 6.84 (d, J = 5.2 Hz, 1H), 6.80-6.75 (m, 2H), 5.64 (d, J = 5.3 Hz, 1H), 5.44-5.34 (m, 1H), 5.07-4.98 (m, 1H), 3.96 (s, 3H), 1.46 (d, J = 7.2 Hz, 3H), 1.42 (d, J = 6.4 Hz, 3H). |
| 31 | 57-68 | 1735, 1510, 1497, 1279, 1249, 1221, 733 cm$^{-1}$ | HRMS-ESI (m/z) [M + Na]$^+$ calcd for C$_{26}$H$_{26}$F$_2$N$_2$O$_4$SNa, 523.1474; found, 523.1488 | $^1$H NMR (500 MHz, CDCl$_3$) δ 12.86 (s, 1H), 10.54 (s, 1H), 7.95 (s, 1H), 7.26 (s, 1H), 7.23-7.17 (m, 2H), 6.94-6.82 (m, 5H), 5.74 (dq, J = 12.5, 6.4 Hz, 1H), 4.99-4.84 (m, 1H), 4.28 (d, J = 10.2 Hz, 1H), 3.97 (s, 3H), 2.36 (s, 3H), 1.29 (d, J = 6.1 Hz, 3H), 1.16 (d, J = 7.2 Hz, 3H).<br>$^{19}$F NMR (471 MHz, CDCl$_3$) δ −115.89, −116.28. |
| 32 | 50-61 | IR (thin film) 3081, 2983, 1737, 1503, 1282, 967, 850, 734 cm$^{-1}$ | HRMS-ESI (m/z) [M + Na]$^+$ calcd for C$_{25}$H$_{22}$F$_4$N$_2$O$_4$SNa, 545.1129; found, 545.1139 | $^1$H NMR (500 MHz, CDCl$_3$) δ 12.84 (s, 1H), 10.54 (s, 1H), 7.92 (s, 1H), 7.35 (td, J = 8.5, 6.1 Hz, 1H), 7.26-7.21 (m, 1H), 6.89-6.76 (m, 4H), 6.73-6.67 (m, 1H), 5.82 (dq, J = 12.1, 6.2 Hz, 1H), 5.05-4.88 (m, 1H), 4.69 (d, J = 9.9 Hz, 1H), 3.97 (s, 3H), 1.31 (d, J = 6.1 Hz, 3H), 1.24 (d, J = 7.1 Hz, 3H). |

TABLE 2-continued

Analytical Data

| Cmpd. No | Melting Point (° C.) | IR (cm$^{-1}$) | MASS SPEC | NMR |
|---|---|---|---|---|
| 33 | 132-141 | IR (thin film) 3092, 2966, 1751, 1512, 1480, 1280, 1132, 908, 798, 732 cm$^{-1}$ | HRMS-ESI (m/z) [M + Na]$^+$ calcd for C$_{22}$H$_{27}$FN$_2$O$_5$SNa, 473.1527; found, 473.1528 | $^1$H NMR (500 MHz, CDCl$_3$) δ 12.86 (s, 1H), 10.60 (s, 1H), 7.95 (s, 1H), 7.17-7.11 (m, 1H), 6.86 (s, 1H), 6.72-6.67 (m, 1H), 6.63 (dt, J = 11.0, 2.4 Hz, 1H), 6.58 (td, J = 8.3, 2.3 Hz, 1H), 5.26 (qd, J = 6.5, 4.0 Hz, 1H), 5.02-4.91 (m, 1H), 4.19 (dd, J = 7.2, 3.9 Hz, 1H), 4.04-3.91 (m, 3H), 2.01-1.92 (m, 1H), 1.41-1.32 (m, 6H), 1.02 (d, J = 3.2 Hz, 3H), 1.00 (d, J = 3.3 Hz, 3H). |
| 34 | | IR (thin film) 2959, 1740, 1513, 1486, 1456, 1282, 1246, 1202, 737 cm$^{-1}$ | HRMS-ESI (m/z) [M + Na]$^+$ calcd for C$_{22}$H$_{28}$N$_2$O$_5$SNa, 455.1611; found, 455.1619 | $^1$H NMR (500 MHz, CDCl$_3$) δ 12.90 (s, 1H), 10.71 (s, 1H), 7.95 (s, 1H), 7.27-7.22 (m, 2H), 6.93 (tt, J = 7.3, 1.1 Hz, 1H), 6.88-6.83 (m, 3H), 5.22 (dt, J = 9.3, 3.8 Hz, 1H), 5.14-5.05 (m, 1H), 4.47 (qd, J = 6.3, 3.9 Hz, 1H), 3.96 (s, 3H), 1.82-1.71 (m, 1H), 1.69-1.64 (m, 1H), 1.62 (d, J = 7.1 Hz, 3H), 1.53-1.35 (m, 2H), 1.33 (d, J = 6.3 Hz, 3H), 0.94 (t, J = 7.4 Hz, 3H). |
| 35 | 45-57 | IR (thin film) 2939, 1737, 1513, 1493, 1274, 1239, 1203, 732 cm$^{-1}$ | HRMS-ESI (m/z) [M + Na]$^+$ calcd for C$_{26}$H$_{27}$FN$_2$O$_5$SNa, 521.1517; found, 521.1530 | $^1$H NMR (500 MHz, CDCl$_3$) δ 12.83 (s, 1H), 10.58 (s, 1H), 7.93 (s, 1H), 7.36 (t, J = 7.3 Hz, 1H), 7.15 (t, J = 7.8 Hz, 2H), 6.91-6.79 (m, 4H), 6.71 (d, J = 8.1 Hz, 2H), 5.40 (d, J = 4.9 Hz, 1H), 5.28-5.19 (m, 1H), 4.99 (s, 1H), 3.96 (s, 3H), 2.50 (s, 3H), 1.43 (d, J = 6.4 Hz, 3H), 1.39 (d, J = 7.3 Hz, 3H). |
| 36 | 141-148 | IR (CDCl3) 3090, 2968, 1752, 1504, 1475, 1199, 800 cm$^{-1}$ | HRMS-ESI (m/z) [M + Na]$^+$ calcd for C$_{22}$H$_{27}$FN$_2$O$_5$SNa, 473.1517; found, 473.1537 | $^1$H NMR (500 MHz, CDCl$_3$) δ 12.91 (s, 1H), 10.75 (s, 1H), 7.95 (s, 1H), 6.99-6.92 (m, 2H), 6.87 (d, J = 5.1 Hz, 1H), 6.85-6.80 (m, 2H), 5.22-5.14 (m, 1H), 5.07 (t, J = 5.7 Hz, 1H), 4.42 (p, J = 6.1 Hz, 1H), 3.97 (s, 3H), 2.12 (pd, J = 6.9, 5.7 Hz, 1H), 1.70 (d, J = 7.2 Hz, 3H), 1.30 (d, J = 6.2 Hz, 3H), 0.98 (d, J = 6.9 Hz, 3H), 0.94 (d, J = 6.7 Hz, 3H). |
| 37 | 125-133 | IR (thin film) 3134, 3093, 2956, 1749, 1509, 1479, 1229, 1209, 798, 731 cm$^{-1}$ | HRMS-ESI (m/z) [M + Na]$^+$ calcd for C$_{23}$H$_{30}$N$_2$O$_5$SNa, 469.1768; found, 469.1773 | $^1$H NMR (500 MHz, CDCl$_3$) δ 12.91 (s, 1H), 10.66 (d, J = 7.6 Hz, 1H), 7.96 (d, J = 5.1 Hz, 1H), 7.02 (d, J = 8.1 Hz, 2H), 6.86 (d, J = 5.2 Hz, 1H), 6.79 (d, J = 8.5 Hz, 2H), 5.22-5.12 (m, 1H), 5.02 (p, J = 7.2 Hz, 1H), 4.36-4.26 (m, 1H), 3.95 (s, 3H), 2.26 (s, 3H), 1.75-1.64 (m, 1H), 1.64-1.51 (m, 2H), 1.48 (d, J = 7.1 Hz, 3H), 1.44-1.38 (m, 1H), 1.36 (d, J = 6.5 Hz, 3H), 0.93 (t, J = 7.2 Hz, 3H). |
| 38 | 49-57 | IR (thin film) 2945, 2868, 1735, 1514, 1487, 1274, 1241, 1205, 733 cm$^{-1}$ | HRMS-ESI (m/z) [M + Na]$^+$ calcd for C$_{24}$H$_{29}$ClN$_2$O$_5$SNa, 515.1378; found, 515.1386 | $^1$H NMR (500 MHz, CDCl$_3$) δ 12.87 (s, 1H), 10.56 (s, 1H), 7.88 (s, 1H), 7.07 (d, J = 9.0 Hz, 2H), 6.97-6.84 (m, 1H), 6.82 (d, J = 9.0 Hz, 2H), 5.18 (qd, J = 6.5, 3.0 Hz, 1H), 4.96 (p, J = 7.1 Hz, 1H), 4.26 (dd, J = 8.4, 2.9 Hz, 1H), 3.97 (s, 3H), 2.12 (h, J = 8.5 Hz, 1H), 1.87-1.49 (m, 8H), 1.40 (d, J = 7.2 Hz, 3H), 1.37 (d, J = 6.5 Hz, 3H). |
| 39 | | | HRMS-ESI (m/z) [M + H]$^+$ calcd for C$_{25}$H$_{25}$F$_2$N$_2$O$_4$S, 487.1498; found, 487.1495 | $^1$H NMR (400 MHz, CDCl$_3$) δ 12.86 (s, 1H), 10.59 (s, 1H), 7.91 (s, 1H), 7.30-7.15 (m, 4H), 7.03-6.90 (m, 4H), 6.86 (d, J = 5.3 Hz, 1H), 5.74 (dq, J = 9.8, 6.2 Hz, 1H), 4.91 (p, J = 7.2 Hz, 1H), 4.06 (d, J = 9.8 Hz, 1H), 3.97 (s, 3H), 1.26 (d, J = 6.1 Hz, 3H), 1.14 (d, J = 7.2 Hz, 3H). $^{19}$F NMR (376 MHz, CDCl$_3$) δ −115.46, −115.84. |

TABLE 2-continued

Analytical Data

| Cmpd. No | Melting Point (° C.) | IR (cm⁻¹) | MASS SPEC | NMR |
|---|---|---|---|---|
| 40 | | IR (thin film) 2957, 1769, 1739, 1493, 1192, 1174, 730 cm⁻¹ | HRMS-ESI (m/z) [M + Na]⁺ calcd for $C_{25}H_{32}N_2NaO_6S$, 511.1873; found, 511.1878 | $^1H$ NMR (400 MHz, $CDCl_3$) δ 9.92 (d, J = 7.0 Hz, 1H), 8.31 (dd, J = 5.5, 1.1 Hz, 1H), 7.30-7.21 (m, 2H), 6.98 (dd, J = 5.5, 0.8 Hz, 1H), 6.93 (tt, J = 7.3, 1.1 Hz, 1H), 6.88-6.77 (m, 2H), 5.29 (dt, J = 10.0, 3.3 Hz, 1H), 5.19 (p, J = 7.1 Hz, 1H), 4.44 (qd, J = 6.3, 3.7 Hz, 1H), 3.90 (s, 3H), 2.35 (s, 3H), 1.80-1.64 (m, 2H), 1.57 (d, J = 7.1 Hz, 3H), 1.46-1.36 (m, 1H), 1.32 (d, J = 6.3 Hz, 3H), 0.95 (d, J = 6.6 Hz, 3H), 0.93 (d, J = 6.5 Hz, 3H). $^{13}C$ NMR (101 MHz, $CDCl_3$) δ 189.37, 171.69, 168.60, 159.83, 157.67, 146.32, 145.23, 136.76, 129.53, 121.19, 116.09, 109.21, 75.11 (2C), 56.42, 52.89, 38.92, 24.44, 23.51, 21.81, 21.23, 16.97, 15.02. |
| 41 | | IR (thin film) 2930, 1769, 1737, 1585, 1492, 1191, 1173, 729 cm⁻¹ | HRMS-ESI (m/z) [M + H]⁺ calcd for $C_{26}H_{35}N_2O_6S$, 503.221; found, 503.227 | $^1H$ NMR (400 MHz, $CDCl_3$) δ 9.93 (d, J = 7.3 Hz, 1H), 8.32 (d, J = 5.5 Hz, 1H), 7.31-7.21 (m, 2H), 6.99 (d, J = 5.5 Hz, 1H), 6.94 (tt, J = 7.4, 1.1 Hz, 1H), 6.92-6.87 (m, 2H), 5.23-5.10 (m, 2H), 4.47 (qd, J = 6.3, 4.4 Hz, 1H), 3.90 (s, 3H), 2.35 (s, 3H), 1.79-1.68 (m, 2H), 1.60 (d, J = 7.2 Hz, 3H), 1.31 (d, J = 6.3 Hz, 3H), 1.30-1.23 (m, 6H), 0.87 (td, J = 5.1, 2.6 Hz, 3H). $^{13}C$ NMR (101 MHz, $CDCl_3$) δ 189.35, 171.60, 168.60, 159.85, 157.72, 146.27, 145.03, 136.87, 129.52, 121.21, 116.28, 109.24, 77.23, 74.74, 56.41, 52.94, 31.55, 29.70, 25.05, 22.45, 21.25, 17.00, 15.67, 13.95. |
| 42 | | IR (thin film) 2931, 1769, 1739, 1492, 1191, 1173, 729 cm⁻¹ | HRMS-ESI (m/z) [M + H]⁺ calcd for $C_{26}H_{34}N_2NaO_6S$, 525.203; found, 525.203 | $^1H$ NMR (400 MHz, $CDCl_3$) δ 10.00-9.87 (m, 1H), 8.31 (d, J = 5.5 Hz, 1H), 7.30-7.19 (m, 2H), 6.98 (d, J = 5.4 Hz, 1H), 6.98-6.89 (m, 1H), 6.90-6.82 (m, 2H), 5.26-5.14 (m, 2H), 4.51-4.40 (m, 1H), 3.90 (s, 3H), 2.35 (s, 3H), 1.79-1.60 (m, 2H), 1.59 (d, J = 7.1 Hz, 3H), 1.52-1.38 (m, 1H), 1.32 (d, J = 6.3 Hz, 3H), 1.33-1.23 (m, 5H), 0.92-0.85 (m, 3H). |
| 43 | | IR (thin film) 2965, 1769, 1734, 1487, 1192, 1174, 730 cm⁻¹ | HRMS-ESI (m/z) [M + H]⁺ calcd for $C_{24}H_{30}ClN_2O_6S$, 509.1508; found, 509.1886 | $^1H$ NMR (400 MHz, $CDCl_3$) δ 9.84 (d, J = 7.2 Hz, 1H), 8.26 (d, J = 5.4 Hz, 1H), 7.13-7.07 (m, 2H), 6.99 (d, J = 5.4 Hz, 1H), 6.85-6.80 (m, 2H), 5.23 (qd, J = 6.4, 3.8 Hz, 1H), 5.04 (p, J = 7.1 Hz, 1H), 4.13 (dd, J = 7.2, 3.9 Hz, 1H), 3.92 (s, 3H), 2.36 (s, 3H), 1.95 (dq, J = 13.7, 6.9 Hz, 1H), 1.36 (d, J = 7.0 Hz, 3H), 1.34 (d, J = 6.2 Hz, 3H), 0.99 (d, J = 6.8 Hz, 6H). |
| 44 | | IR (thin film) 2939, 1769, 1735, 1501, 1193, 1176, 730 cm⁻¹ | HRMS-ESI (m/z) [M + H]⁺ calcd for $C_{28}H_{30}FN_2O_6S$, 541.1803; found, 541.1859 | $^1H$ NMR (400 MHz, $CDCl_3$) δ 9.75 (d, J = 6.5 Hz, 1H), 8.31 (dd, J = 5.4, 1.5 Hz, 1H), 7.38-7.32 (m, 2H), 7.23 (dd, J = 8.4, 6.8 Hz, 2H), 7.20-7.07 (m, 2H), 6.97 (dd, J = 5.5, 1.1 Hz, 1H), 6.66-6.53 (m, 2H), 5.87 (dq, J = 9.8, 6.2 Hz, 1H), 4.99 (p, J = 7.1 Hz, 1H), 4.56 (d, J = 10.0 Hz, 1H), 3.89 (s, 3H), 3.83 (s, 3H), 2.34 (s, 3H), 1.26 (d, J = 6.2 Hz, 3H), 0.98 (d, J = 7.2 Hz, 3H). |
| 45 | | IR (thin film) 2938, 1769, 1733, 1500, 1192, 1175, 729 cm⁻¹ | HRMS-ESI (m/z) [M + H]⁺ calcd for $C_{29}H_{32}FN_2O_6S$, 555.196; found, 555.2033 | $^1H$ NMR (400 MHz, $CDCl_3$) δ 9.76 (d, J = 7.3 Hz, 1H), 8.31 (d, J = 5.5 Hz, 1H), 7.24-7.18 (m, 2H), 7.15 (dd, J = 8.8, 6.7 Hz, 1H), 7.04 (d, J = 7.9 Hz, 2H), 6.97 (d, J = 5.5 Hz, 1H), 6.59-6.50 (m, 2H), 5.84 (dq, J = 9.8, 6.2 Hz, 1H), 5.00 (p, J = 7.1 Hz, 1H), 4.52 (d, J = 9.8 Hz, 1H), 3.89 (s, 3H), 3.83 |

TABLE 2-continued

Analytical Data

| Cmpd. No | Melting Point (° C.) | IR (cm$^{-1}$) | MASS SPEC | NMR |
|---|---|---|---|---|
| | | | | (s, 3H), 2.34 (s, 3H), 2.25 (s, 3H), 1.24 (d, J = 6.2 Hz, 3H), 1.02 (d, J = 7.1 Hz, 3H). |
| 46 | | IR (thin film) 2981, 1769, 1735, 1496, 1192, 1174, 730 cm$^{-1}$ | HRMS-ESI (m/z) [M + H]$^+$ calcd for C$_{29}$H$_{32}$FN$_2$O$_5$S, 539.201; found, 539.2077 | $^1$H NMR (400 MHz, CDCl$_3$) δ 9.74 (d, J = 7.5 Hz, 1H), 8.32 (d, J = 5.4 Hz, 1H), 7.29 (dd, J = 8.7, 5.8 Hz, 1H), 7.15 (d, J = 8.1 Hz, 2H), 7.03 (d, J = 7.9 Hz, 2H), 6.98 (d, J = 5.5 Hz, 1H), 6.91-6.81 (m, 2H), 5.77 (dq, J = 10.2, 6.1 Hz, 1H), 4.99 (p, J = 7.2 Hz, 1H), 4.26 (d, J = 10.3 Hz, 1H), 3.90 (s, 3H), 2.38 (s, 3H), 2.34 (s, 3H), 2.25 (s, 3H), 1.27 (d, J = 6.1 Hz, 3H), 1.03 (d, J = 7.1 Hz, 3H). |
| 47 | | IR (thin film) 3283, 2982, 1769, 1737, 1491, 1193, 1175, 1091, 732 cm$^{-1}$ | HRMS-ESI (m/z) [M + H]$^+$ calcd for C$_{27}$H$_{27}$Cl$_2$N$_2$O$_5$S, 561.1012; found, 561.107 | $^1$H NMR (400 MHz, CDCl$_3$) δ 9.77 (d, J = 7.3 Hz, 1H), 8.31 (d, J = 5.5 Hz, 1H), 7.30-7.13 (m, 8H), 6.99 (d, J = 5.5 Hz, 1H), 5.75 (dq, J = 9.6, 6.2 Hz, 1H), 5.06-4.95 (m, 1H), 4.04 (d, J = 9.7 Hz, 1H), 3.90 (s, 3H), 2.34 (s, 3H), 1.25 (d, J = 6.2 Hz, 3H), 1.08 (d, J = 7.2 Hz, 3H). $^{13}$C NMR (101 MHz, CDCl$_3$) δ 189.35, 171.28, 168.59, 159.86, 146.26, 144.93, 139.32, 139.18, 136.87, 133.04, 132.80, 129.49, 129.40, 129.05, 128.77, 109.27, 72.99, 56.42, 56.37, 52.79, 21.24, 19.12, 16.29. |
| 48 | | IR (thin film) 2937, 1769, 1734, 1500, 1438, 1310, 1192, 1175, 730 cm$^{-1}$ | HRMS-ESI (m/z) [M + H]$^+$ calcd for C$_{31}$H$_{27}$N$_2$O$_5$S, 549.2418; found, 549.2448 | $^1$H NMR (400 MHz, CDCl$_3$) δ 9.75 (d, J = 7.3 Hz, 1H), 8.31 (d, J = 5.4 Hz, 1H), 7.19 (d, J = 7.8 Hz, 1H), 7.12 (d, J = 7.8 Hz, 1H), 6.97 (d, J = 5.5 Hz, 1H), 6.96-6.86 (m, 4H), 5.71 (dq, J = 10.1, 6.1 Hz, 1H), 4.98 (p, J = 7.1 Hz, 1H), 4.46 (d, J = 10.0 Hz, 1H), 3.90 (s, 3H), 2.36 (s, 3H), 2.34 (s, 3H), 2.31 (s, 3H), 2.25 (s, 3H), 2.22 (s, 3H), 1.31 (d, J = 6.1 Hz, 3H), 1.05 (d, J = 7.1 Hz, 3H). |
| 49 | | IR (thin film) 2984, 1767, 1738, 1477, 1192, 1175, 1102, 730 cm$^{-1}$ | HRMS-ESI (m/z) [M + H]$^+$ calcd for C$_{27}$H$_{27}$Cl$_2$N$_2$O$_6$S, 577.0961; found, 577.0987 | $^1$H NMR (300 MHz, CDCl$_3$) δ 9.89 (d, J = 7.2 Hz, 1H), 8.26 (dd, J = 5.4, 0.9 Hz, 1H), 7.44-7.27 (m, 6H), 6.97 (dd, J = 5.5, 0.6 Hz, 1H), 6.92 (dd, J = 8.9, 2.5 Hz, 1H), 6.56 (d, J = 8.9 Hz, 1H), 5.34 (qd, J = 6.4, 4.6 Hz, 1H), 5.24 (d, J = 4.6 Hz, 1H), 5.10 (p, J = 7.2 Hz, 1H), 3.90 (s, 3H), 2.34 (s, 3H), 1.43 (d, J = 6.5 Hz, 3H), 1.40 (d, J = 7.2 Hz, 3H). |
| 50 | | IR (thin film) 3276, 2981, 1769, 1734, 1509, 1192, 1175, 729 cm$^{-1}$ | HRMS-ESI (m/z) [M + H]$^+$ calcd for C$_{29}$H$_{33}$N$_2$O$_5$S, 521.2105; found, 521.2127 | $^1$H NMR (300 MHz, CDCl$_3$) δ 9.77 (d, J = 7.4 Hz, 1H), 8.31 (d, J = 5.5 Hz, 1H), 7.22-7.11 (m, 4H), 7.11-7.01 (m, 4H), 6.97 (d, J = 5.5 Hz, 1H), 5.80 (dq, J = 10.0, 6.2 Hz, 1H), 4.98 (p, J = 7.0 Hz, 1H), 3.99 (d, J = 10.2 Hz, 1H), 3.89 (s, 3H), 2.34 (d, J = 2.8 Hz, 3H), 2.27 (s, 3H), 2.25 (s, 3H), 1.25 (d, J = 6.2 Hz, 3H), 0.99 (d, J = 7.2 Hz, 3H). |
| 51 | | IR (thin film) 2982, 1768, 1734, 1508, 1192, 1174, 728 cm$^{-1}$ | HRMS-ESI (m/z) [M + H]$^+$ calcd for C$_{27}$H$_{28}$FN$_2$O$_5$S, 511.1697; found, 511.1723 | $^1$H NMR (400 MHz, CDCl$_3$) δ 9.76 (d, J = 7.2 Hz, 1H), 8.32 (d, J = 5.5 Hz, 1H), 7.34-7.20 (m, 6H), 7.19-7.13 (m, 1H), 7.03-6.94 (m, 3H), 5.80 (dq, J = 10.0, 6.2 Hz, 1H), 4.98 (p, J = 7.1 Hz, 1H), 4.06 (d, J = 10.1 Hz, 1H), 3.90 (s, 3H), 2.34 (s, 3H), 1.26 (d, J = 6.1 Hz, 3H), 0.97 (d, J = 7.1 Hz, 3H). $^{19}$F NMR (376 MHz, CDCl$_3$) δ −115.80. |

TABLE 2-continued

Analytical Data

| Cmpd. No | Melting Point (° C.) | IR (cm$^{-1}$) | MASS SPEC | NMR |
|---|---|---|---|---|
| 52 | | IR (thin film) 2940, 1769, 1734, 1591, 1489, 1193, 1176, 732 cm$^{-1}$ | HRMS-ESI (m/z) [M + H]$^+$ calcd for C$_{29}$H$_{31}$Cl$_2$N$_2$O$_7$S, 621.1224; found, 621.1836 | $^1$H NMR (400 MHz, CDCl$_3$) δ 9.79 (d, J = 7.4 Hz, 1H), 8.31 (dd, J = 5.4, 1.1 Hz, 1H), 7.34 (d, J = 8.3 Hz, 1H), 7.10 (d, J = 8.0 Hz, 1H), 6.98 (d, J = 5.4 Hz, 1H), 6.87-6.80 (m, 3H), 6.77 (d, J = 2.1 Hz, 1H), 5.91 (dq, J = 9.6, 6.2 Hz, 1H), 5.01 (p, J = 7.1 Hz, 1H), 4.84 (d, J = 9.6 Hz, 1H), 3.90 (s, 3H), 3.83 (s, 3H), 3.75 (s, 3H), 2.34 (s, 3H), 1.23 (d, J = 6.2 Hz, 3H), 1.10 (d, J = 7.1 Hz, 3H). |
| 53 | | IR (thin film) 2938, 1768, 1736, 1623, 1584, 1505, 1193, 1175, 1155, 729 cm$^{-1}$ | HRMS-ESI (m/z) [M + H]$^+$ calcd for C$_{29}$H$_{31}$F$_2$N$_2$O$_7$S, 589.1815; found, 589.1836 | $^1$H NMR (400 MHz, CDCl$_3$) δ 9.80 (d, J = 7.3 Hz, 1H), 8.31 (d, J = 5.5 Hz, 1H), 7.30 (t, J = 8.6 Hz, 1H), 7.17 (t, J = 8.5 Hz, 1H), 6.98 (d, J = 5.4 Hz, 1H), 6.66-6.56 (m, 3H), 6.53 (dd, J = 12.1, 2.6 Hz, 1H), 5.82 (dq, J = 12.2, 6.2 Hz, 1H), 5.04 (p, J = 7.1 Hz, 1H), 4.63 (d, J = 10.2 Hz, 1H), 3.90 (s, 3H), 3.75 (s, 3H), 3.73 (s, 3H), 2.34 (s, 3H), 1.29 (d, J = 6.1 Hz, 3H), 1.13 (d, J = 7.1 Hz, 3H). |
| 54 | | IR (thin film) 2937, 1768, 1732, 1491, 1192, 1176, 730 cm$^{-1}$ | HRMS-ESI (m/z) [M + H]$^+$ calcd for C$_{29}$H$_{33}$N$_2$O$_7$S, 553.2003; found, 553.2026 | $^1$H NMR (400 MHz, CDCl$_3$) δ 9.78 (d, J = 7.5 Hz, 1H), 8.31 (d, J = 5.5 Hz, 1H), 7.47 (dd, J = 7.7, 1.7 Hz, 1H), 7.26 (dd, J = 8.0, 1.7 Hz, 1H), 7.13 (dddd, J = 10.1, 8.1, 5.2, 1.7 Hz, 2H), 6.96 (d, J = 5.5 Hz, 1H), 6.90-6.81 (m, 3H), 6.78 (dt, J = 8.3, 1.8 Hz, 1H), 5.99 (dq, J = 9.9, 6.1 Hz, 1H), 5.03-4.98 (m, 2H), 3.88 (d, J = 0.8 Hz, 3H), 3.84 (s, 3H), 3.76 (s, 3H), 2.34 (s, 3H), 1.26 (d, J = 6.2 Hz, 3H), 1.00 (d, J = 7.1 Hz, 3H). |
| 55 | | IR (thin film) 2982, 1768, 1734, 1506, 1222, 1193, 1176, 730 cm$^{-1}$ | HRMS-ESI (m/z) [M + H]$^+$ calcd for C$_{27}$H$_{27}$F$_2$N$_2$O$_5$S, 529.1603; found, 529.1658 | $^1$H NMR (400 MHz, CDCl$_3$) δ 9.72 (d, J = 7.1 Hz, 1H), 8.32 (dt, J = 5.4, 1.1 Hz, 1H), 7.25-7.14 (m, 4H), 7.05-6.88 (m, 5H), 5.68 (dq, J = 8.9, 6.2 Hz, 1H), 4.97 (p, J = 7.2 Hz, 1H), 4.05 (d, J = 8.9 Hz, 1H), 3.91 (s, 3H), 2.35 (s, 3H), 1.39 (d, J = 7.2 Hz, 3H), 1.21 (d, J = 6.2 Hz, 3H). |
| 56 | | IR (thin film) 2966, 1769, 1741, 1507, 1191, 1174, 730 cm$^{-1}$ | HRMS-ESI (m/z) [M + H]$^+$ calcd for C$_{25}$H$_{33}$N$_2$O$_6$S, 489.2054; found, 489.2116 | $^1$H NMR (400 MHz, CDCl$_3$) δ 9.97 (d, J = 7.4 Hz, 1H), 8.32 (d, J = 5.5 Hz, 1H), 7.10-7.03 (m, 2H), 6.99 (d, J = 5.5 Hz, 1H), 6.80-6.73 (m, 2H), 5.26 (p, J = 7.1 Hz, 1H), 5.07 (dd, J = 6.3, 5.2 Hz, 1H), 4.46 (p, J = 6.2 Hz, 1H), 3.91 (s, 3H), 2.36 (s, 3H), 2.27 (s, 3H), 2.21-2.09 (m, 1H), 1.66 (d, J = 7.1 Hz, 3H), 1.29 (d, J = 6.2 Hz, 3H), 0.97 (d, J = 7.0 Hz, 3H), 0.93 (d, J = 6.7 Hz, 3H). |
| 57 | | IR (thin film) 2983, 1768, 1739, 1481, 1192, 1175, 731 cm$^{-1}$ | HRMS-ESI (m/z) [M + H]$^+$ calcd for C$_{27}$H$_{28}$ClN$_2$O$_6$S, 543.1351; found, 543.1382 | $^1$H NMR (400 MHz, CDCl$_3$) δ 9.86 (d, J = 1.1 Hz, 1H), 8.28 (dd, J = 5.4, 0.9 Hz, 1H), 7.45-7.37 (m, 2H), 7.36-7.27 (m, 4H), 7.02-6.93 (m, 2H), 6.81 (td, J = 7.6, 1.4 Hz, 1H), 6.67 (dd, J = 8.3, 1.4 Hz, 1H), 5.41-5.32 (m, 1H), 5.28 (d, J = 4.8 Hz, 1H), 5.13 (p, J = 7.1 Hz, 1H), 3.89 (s, 3H), 2.34 (s, 3H), 1.46 (s, 3H), 1.35 (d, J = 6.4 Hz, 3H), 1.35 (d, J = 7.2 Hz, 3H). |
| 58 | | IR (thin film) 2966, 1770, 1742, 1505, 1193, 1177, 736 cm$^{-1}$ | HRMS-ESI (m/z) [M + Na]$^+$ calcd for C$_{25}$H$_{32}$N$_2$NaO$_7$S, 527.1822; found, 527.191 | $^1$H NMR (400 MHz, CDCl$_3$) δ 9.98 (d, J = 7.4 Hz, 1H), 8.32 (dd, J = 5.5, 0.9 Hz, 1H), 6.99 (d, J = 5.5 Hz, 1H), 6.89-6.76 (m, 4H), 5.27 (p, J = 7.2 Hz, 1H), 5.06 (t, J = 5.8 Hz, 1H), 4.38 (p, J = 6.1 Hz, 1H), 3.90 (s, 3H), 3.76 (s, 3H), 2.36 (s, 3H), 2.25-2.01 (m, 1H), 1.66 (d, J = 7.1 Hz, 3H), 1.28 (d, J = 6.1 Hz, 3H), 0.96 (d, J = 6.9 Hz, 3H), 0.94 (d, J = 6.8 Hz, 3H). |

TABLE 2-continued

Analytical Data

| Cmpd. No | Melting Point (° C.) | IR (cm⁻¹) | MASS SPEC | NMR |
|---|---|---|---|---|
| 59 | | IR (thin film) 1769, 1734, 1507, 1193, 1176, 732 cm⁻¹ | HRMS-ESI (m/z) [M + H]⁺ calcd for $C_{27}H_{27}F_2N_2O_5S$, 529.1603; found, 529.1654 | ¹H NMR (400 MHz, CDCl₃) δ 9.71 (d, J = 7.3 Hz, 1H), 8.32 (dd, J = 5.4, 1.0 Hz, 1H), 7.26-7.12 (m, 4H), 7.04-6.87 (m, 5H), 5.68 (dq, J = 9.0, 6.2 Hz, 1H), 4.97 (p, J = 7.1 Hz, 1H), 4.05 (d, J = 9.0 Hz, 1H), 3.92 (s, 3H), 2.35 (s, 3H), 1.39 (d, J = 7.2 Hz, 3H), 1.21 (d, J = 6.2 Hz, 3H). |
| 60 | | IR (thin film) 3981, 1768, 1736, 1585, 1491, 1310, 1191, 1173, 728 cm⁻¹ | HRMS-ESI (m/z) [M + H]⁺ calcd for $C_{24}H_{29}N_2O_6S$, 473.1741; found, 473.177 | ¹H NMR (400 MHz, CDCl₃) δ 9.88 (d, J = 7.4 Hz, 1H), 8.29 (d, J = 5.5 Hz, 1H), 7.29-7.19 (m, 2H), 6.98 (d, J = 5.5 Hz, 1H), 6.96-6.88 (m, 3H), 5.86 (ddt, J = 17.1, 10.1, 7.1 Hz, 1H), 5.22-5.04 (m, 4H), 4.42 (ddd, J = 6.9, 5.3, 4.0 Hz, 1H), 3.90 (s, 3H), 2.57-2.38 (m, 2H), 2.35 (s, 3H), 1.46 (d, J = 7.2 Hz, 3H), 1.38 (d, J = 6.5 Hz, 3H). |
| 61 | | IR (thin film) 2966, 1769, 1740, 1585, 1492, 1191, 1173, 728 cm⁻¹ | HRMS-ESI (m/z) [M + H]⁺ calcd for $C_{24}H_{31}N_2O_6S$, 475.1897; found, 475.1979 | ¹H NMR (400 MHz, CDCl₃) δ 9.98 (d, J = 7.3 Hz, 1H), 8.32 (dd, J = 5.4, 1.2 Hz, 1H), 7.29-7.24 (m, 2H), 6.99 (dd, J = 5.5, 0.8 Hz, 1H), 6.94 (tt, J = 7.3, 1.1 Hz, 1H), 6.91-6.85 (m, 2H), 5.27 (p, J = 7.2 Hz, 1H), 5.09 (dd, J = 6.2, 5.2 Hz, 1H), 4.51 (p, J = 6.2 Hz, 1H), 3.90 (s, 3H), 2.36 (s, 3H), 2.20-2.10 (m, 1H), 1.66 (d, J = 7.1 Hz, 3H), 1.31 (d, J = 6.2 Hz, 3H), 0.98 (d, J = 7.0 Hz, 3H), 0.93 (d, J = 6.8 Hz, 3H). |
| 62 | | IR (thin film) 2959, 1770, 1737, 1507, 1311, 1192, 1175, 1104, 822, 732 cm⁻¹ | HRMS-ESI (m/z) [M + Na]⁺ calcd for $C_{25}H_{32}N_2O_6SNa$, 511.1873; found, 511.1874 | ¹H NMR (500 MHz, CDCl₃) δ 9.88 (d, J = 7.3 Hz, 1H), 8.30 (d, J = 5.4 Hz, 1H), 7.02 (d, J = 7.9 Hz, 2H), 6.98 (d, J = 5.5 Hz, 1H), 6.79 (d, J = 8.5 Hz, 2H), 5.20-5.08 (m, 2H), 4.30 (dt, J = 7.9, 3.8 Hz, 1H), 3.90 (s, 3H), 2.35 (s, 3H), 2.26 (s, 3H), 1.77-1.65 (m, 1H), 1.63-1.49 (m, 2H), 1.44 (d, J = 7.1 Hz, 3H), 1.43-1.37 (m, 1H), 1.34 (d, J = 6.5 Hz, 3H), 0.93 (t, J = 7.2 Hz, 3H). |
| 63 | | IR (thin film) 2984, 1769, 1738, 1604, 1502, 1282, 967, 909, 849, 732 cm⁻¹ | HRMS-ESI (m/z) [M + Na]⁺ calcd for $C_{27}H_{24}F_4N_2O_5SNa$, 587.1234; found, 587.1243 | ¹H NMR (500 MHz, CDCl₃) δ 9.80 (d, J = 7.3 Hz, 1H), 8.31 (d, J = 5.4 Hz, 1H), 7.41-7.31 (m, 1H), 7.28-7.20 (m, 1H), 6.99 (d, J = 5.5 Hz, 1H), 6.86-6.77 (m, 3H), 6.76-6.71 (m, 1H), 5.83 (dq, J = 12.2, 6.2 Hz, 1H), 5.03 (p, J = 7.2 Hz, 1H), 4.69 (d, J = 9.9 Hz, 1H), 3.91 (s, 3H), 2.35 (s, 3H), 1.30 (d, J = 6.1 Hz, 3H), 1.16 (d, J = 7.1 Hz, 3H). |
| 64 | | IR (thin film) 2982, 1769, 1736, 1497, 1193, 1175, 910, 732 cm⁻¹ | HRMS-ESI (m/z) [M + H]⁺ calcd for $C_{28}H_{29}F_2N_2O_5S$, 543.1760; found, 543.1845 | ¹H NMR (500 MHz, CDCl₃) δ 9.75 (d, J = 7.3 Hz, 1H), 8.32 (d, J = 5.4 Hz, 1H), 7.28-7.21 (m, 3H), 6.99 (d, J = 5.5 Hz, 1H), 6.96-6.83 (m, 4H), 5.74 (dq, J = 10.2, 6.1 Hz, 1H), 5.05-4.96 (m, 1H), 4.28 (d, J = 10.2 Hz, 1H), 3.90 (s, 3H), 2.36 (s, 3H), 2.34 (s, 3H), 1.28 (d, J = 6.1 Hz, 3H), 1.08 (d, J = 7.1 Hz, 3H). |
| 65 | | IR (thin film) 2936, 1770, 1734, 1505, 1193, 1177, 1040, 911, 733 cm⁻¹ | HRMS-ESI (m/z) [M + Na]⁺ calcd for $C_{31}H_{36}N_2O_7SNa$, 603.2135; found, 603.2132 | ¹H NMR (500 MHz, CDCl₃) δ 9.77 (d, J = 7.3 Hz, 1H), 8.31 (d, J = 5.4 Hz, 1H), 7.32 (d, J = 7.8 Hz, 1H), 7.11 (d, J = 8.2 Hz, 1H), 6.97 (d, J = 5.5 Hz, 1H), 6.67 (d, J = 7.9 Hz, 1H), 6.65-6.63 (m, 2H), 6.61-6.57 (m, 1H), 5.94 (dq, J = 9.9, 6.2 Hz, 1H), 5.05-4.96 (m, 1H), 4.91 (d, J = 9.8 Hz, 1H), 3.90 (s, 3H), 3.82 (s, 3H), 3.74 (s, 3H), 2.34 (s, 3H), 2.27 (s, 3H), 2.25 (s, 3H), 1.24 (d, J = 6.2 Hz, 3H), 1.03 (d, J = 7.1 Hz, 3H). |

TABLE 2-continued

Analytical Data

| Cmpd. No | Melting Point (° C.) | IR (cm⁻¹) | MASS SPEC | NMR |
|---|---|---|---|---|
| 66 | | IR (thin film) 2974, 1769, 1740, 1586, 1492, 1192, 1175, 1103, 732 cm⁻¹ | HRMS-ESI (m/z) [M + Na]⁺ calcd for $C_{23}H_{28}N_2O_6SNa$, 483.1560; found, 483.1556 | ¹H NMR (500 MHz, CDCl₃) δ 9.92 (d, J = 7.3 Hz, 1H), 8.32 (d, J = 5.5 Hz, 1H), 7.29-7.22 (m, 2H), 6.98 (d, J = 5.5 Hz, 1H), 6.93 (tt, J = 7.4, 1.1 Hz, 1H), 6.89-6.83 (m, 2H), 5.27-5.17 (m, 1H), 5.13 (td, J = 6.5, 4.2 Hz, 1H), 4.47 (qd, J = 6.3, 4.2 Hz, 1H), 3.91 (s, 3H), 2.36 (s, 3H), 1.81-1.70 (m, 2H), 1.60 (d, J = 7.2 Hz, 3H), 1.33 (d, J = 6.3 Hz, 3H), 0.97 (t, J = 7.4 Hz, 3H). |
| 67 | | IR (thin film) 2939, 1769, 1735, 1599, 1500, 1279, 1193, 1176, 733 cm⁻¹ | HRMS-ESI (m/z) [M + Na]⁺ calcd for $C_{29}H_{30}F_2N_2O_7SNa$, 611.1634; found, 611.1643 | ¹H NMR (500 MHz, CDCl₃) δ 9.78 (d, J = 7.4 Hz, 1H), 8.31 (d, J = 5.4 Hz, 1H), 7.38 (dd, J = 8.5, 6.7 Hz, 1H), 7.14 (dd, J = 8.3, 6.7 Hz, 1H), 6.98 (d, J = 5.5 Hz, 1H), 6.62-6.47 (m, 4H), 5.92 (dq, J = 9.7, 6.2 Hz, 1H), 5.08-4.96 (m, 1H), 4.84 (d, J = 9.7 Hz, 1H), 3.90 (s, 3H), 3.83 (s, 3H), 3.74 (s, 3H), 2.34 (s, 3H), 1.23 (d, J = 6.2 Hz, 3H), 1.08 (d, J = 7.1 Hz, 3H). |
| 68 | | | HRMS-ESI (m/z) [M + Na]⁺ calcd for $C_{27}H_{26}F_2N_2O_5SNa$, 551.1423; found, 551.143 | ¹H NMR (500 MHz, CDCl₃) δ 9.77 (d, J = 7.3 Hz, 1H), 8.32 (d, J = 5.4 Hz, 1H), 7.28-7.19 (m, 4H), 7.02-6.92 (m, 5H), 5.75 (dq, J = 9.8, 6.2 Hz, 1H), 5.04-4.96 (m, 1H), 4.05 (d, J = 9.7 Hz, 1H), 3.90 (s, 3H), 2.34 (s, 3H), 1.25 (d, J = 6.2 Hz, 3H), 1.06 (d, J = 7.2 Hz, 3H). ¹⁹F NMR (471 MHz, CDCl₃) δ −115.46--115.56 (m), −115.81--115.92 (m). |
| 69 | | IR (thin film) 2967, 1769, 1742, 1586, 1492, 1192, 1174, 909, 730 cm⁻¹ | HRMS-ESI (m/z) [M + Na]⁺ calcd for $C_{24}H_{30}N_2O_6SNa$, 497.1717; found, 497.1723 | ¹H NMR (500 MHz, CDCl₃) δ 9.95 (d, J = 7.4 Hz, 1H), 8.33 (d, J = 5.4 Hz, 1H), 7.29-7.22 (m, 3H), 6.99 (d, J = 5.4 Hz, 1H), 6.94 (tt, 7 = 7.3, 1.1 Hz, 1H), 6.85 (dt, J = 7.8, 1.1 Hz, 2H), 5.31-5.21 (m, 1H), 5.09 (dd, J = 7.0, 5.0 Hz, 1H), 4.55 (qd, J = 6.2, 4.9 Hz, 1H), 3.91 (s, 3H), 2.36 (s, 3H), 1.68 (d, J = 7.2 Hz, 3H), 1.32 (d, J = 6.3 Hz, 3H), 1.00 (d, J = 6.9 Hz, 3H), 0.96 (d, J = 6.7 Hz, 3H). |
| 70 | | | HRMS-ESI (m/z) [M + Na]⁺ calcd for $C_{28}H_{28}F_2N_2O_6SNa$, 581.1528; found, 581.1535 | ¹H NMR (500 MHz, CDCl₃) δ 9.78 (d, J = 7.4 Hz, 1H), 8.32 (d, J = 5.5 Hz, 1H), 7.32-7.18 (m, 3H), 6.98 (d, J = 5.5 Hz, 1H), 6.95 (t, J = 8.7 Hz, 2H), 6.60 (td, J = 8.3, 2.6 Hz, 1H), 6.54 (dd, J = 10.9, 2.5 Hz, 1H), 5.79 (dq, J = 10.0, 6.1 Hz, 1H), 5.05-4.97 (m, 1H), 4.52 (d, J = 10.2 Hz, 1H), 3.90 (s, 3H), 3.77 (s, 3H), 2.34 (s, 3H), 1.23 (d, J = 6.2 Hz, 3H), 1.07 (d, J = 7.1 Hz, 3H). ¹⁹F NMR (471 MHz, CDCl₃) δ −113.15--113.26 (m), −116.00--116.12 (m). |
| 71 | | IR (thin film) 2944, 1769, 1735, 1487, 1280, 1239, 1193, 1175, 731 cm⁻¹ | HRMS-ESI (m/z) [M + Na]⁺ calcd for $C_{26}H_{31}ClN_2O_6SNa$, 557.1484; found, 557.1494 | ¹H NMR (500 MHz, CDCl₃) δ 9.84 (d, J = 7.3 Hz, 1H), 8.24 (d, J = 5.5 Hz, 1H), 7.08 (d, J = 9.0 Hz, 2H), 6.99 (d, J = 5.5 Hz, 1H), 6.82 (d, J = 9.0 Hz, 2H), 5.22-5.11 (m, 1H), 5.05 (p, J = 7.2 Hz, 1H), 4.25 (dd, J = 8.4, 2.9 Hz, 1H), 3.92 (s, 3H), 2.36 (s, 3H), 2.12 (h, J = 8.1 Hz, 1H), 1.88-1.43 (m, 8H), 1.36 (d, J = 1.7 Hz, 3H), 1.35 (d, J = 1.0 Hz, 3H). |
| 72 | | IR (thin film) 2982, 1769, 1735, 1496, 1194, 1175, 909, 732, 700 cm⁻¹ | HRMS-ESI (m/z) [M + Na]⁺ calcd for $C_{28}H_{29}FN_2O_5SNa$, 547.1673 found, 547.1681 | ¹H NMR (500 MHz, CDCl₃) δ 9.73 (d, J = 7.3 Hz, 1H), 8.32 (d, J = 5.5 Hz, 1H), 7.34-7.26 (m, 3H), 7.25-7.20 (m, 2H), 7.17-7.12 (m, 1H), 6.98 (d, J = 5.5 Hz, 1H), 6.89 (td, J = 8.4, 2.8 Hz, 1H), 6.85 (dd, J = 9.7, 2.8 Hz, 1H), 5.80 (dq, J = 10.3, 6.1 Hz, 1H), |

TABLE 2-continued

Analytical Data

| Cmpd. No | Melting Point (° C.) | IR (cm$^{-1}$) | MASS SPEC | NMR |
|---|---|---|---|---|
| | | | | 5.07-4.93 (m, 1H), 4.30 (d, J = 10.4 Hz, 1H), 3.90 (s, 3H), 2.40 (s, 3H), 2.34 (s, 3H), 1.28 (d, J = 6.1 Hz, 3H), 0.99 (d, J = 7.2 Hz, 3H). |
| 73 | | IR (thin film) 2968, 1770, 1742, 1503, 1194, 1176, 827, 733 cm$^{-1}$ | HRMS-ESI (m/z) [M + H]$^+$ calcd for C$_{24}$H$_{30}$FN$_2$O$_6$S, 493.180; found, 493.1121 | $^1$H NMR (500 MHz, CDCl$_3$) δ 9.96 (d, J = 7.4 Hz, 1H), 8.33 (d, J = 5.4 Hz, 1H), 6.99 (d, J = 5.5 Hz, 1H), 6.98-6.92 (m, 2H), 6.85-6.79 (m, 2H), 5.33-5.22 (m, 1H), 5.06 (t, J = 5.7 Hz, 1H), 4.42 (p, J = 6.2 Hz, 1H), 3.91 (s, 3H), 2.36 (s, 3H), 2.16-2.07 (m, 1H), 1.66 (d, J = 7.0 Hz, 3H), 1.29 (d, J = 6.2 Hz, 3H), 0.97 (d, J = 6.9 Hz, 3H), 0.93 (d, J = 6.8 Hz, 3H). |
| 74 | | IR (thin film) 3281, 2941, 1769, 1739, 1588, 1494, 1194, 1176, 732 cm$^{-1}$ | HRMS-ESI (m/z) [M + Na]$^+$ calcd for C$_{28}$H$_{29}$FN$_2$O$_6$SNa, 563.1623; found, 563.1633 | $^1$H NMR (500 MHz, CDCl$_3$) δ 9.85 (d, J = 7.3 Hz, 1H), 8.27 (d, 7 = 5.4 Hz, 1H), 7.38 (dd, J = 8.6, 5.9 Hz, 1H), 7.21-7.12 (m, 2H), 6.96 (d, J = 5.5 Hz, 1H), 6.91-6.81 (m, 3H), 6.74 (d, J = 7.8 Hz, 2H), 5.39 (d, J = 5.0 Hz, 1H), 5.23 (qd, J = 6.4, 5.0 Hz, 1H), 5.15-5.06 (m, 1H), 3.90 (s, 3H), 2.50 (s, 3H), 2.35 (s, 3H), 1.44 (d, J = 6.4 Hz, 3H), 1.31 (d, J = 7.1 Hz, 3H). |
| 75 | | | HRMS-ESI (m/z) [M + H]$^+$ calcd for C$_{27}$H$_{27}$ClFN$_2$O$_6$S, 561.1257; found, 561.1348 | $^1$H NMR (500 MHz, CDCl$_3$) δ 9.86 (d, J = 7.4 Hz, 1H), 8.28 (d, J = 5.5 Hz, 1H), 7.48 (dd, J = 8.8, 6.1 Hz, 1H), 7.22-7.16 (m, 2H), 7.12 (dd, J = 8.4, 2.6 Hz, 1H), 6.97 (d, J = 5.5 Hz, 1H), 6.96-6.87 (m, 2H), 6.79 (dd, J = 8.8, 1.1 Hz, 2H), 5.64 (d, J = 5.5 Hz, 1H), 5.45-5.31 (m, 1H), 5.30-5.00 (m, 1H), 3.90 (s, 3H), 2.35 (s, 3H), 1.42 (d, J = 6.4 Hz, 3H), 1.39 (d, J = 7.1 Hz, 3H). <br> $^{19}$F NMR (471 MHz, CDCl$_3$) δ −109.42--116.80 (m). |
| 76 | | IR (thin film) 2960, 1770, 1740, 1586, 1493, 1193, 1175, 1108, 732 cm$^{-1}$ | HRMS-ESI (m/z) [M + Na]$^+$ calcd for C$_{24}$H$_{30}$N$_2$O$_6$SNa, 497.1717; found, 497.1715 | $^1$H NMR (500 MHz, CDCl$_3$) δ 9.92 (d, J = 7.3 Hz, 1H), 8.32 (d, J = 5.4 Hz, 1H), 7.30-7.21 (m, 2H), 6.98 (d, J = 5.5 Hz, 1H), 6.93 (tt, J = 7.3, 1.1 Hz, 1H), 6.88-6.85 (m, 2H), 5.27-5.14 (m, 2H), 4.46 (qd, J = 6.3, 4.0 Hz, 1H), 3.91 (s, 3H), 2.35 (s, 3H), 1.80-1.60 (m, 2H), 1.58 (d, J = 7.1 Hz, 3H), 1.51-1.34 (m, 2H), 1.32 (d, J = 6.3 Hz, 3H), 0.94 (t, J = 7.4 Hz, 3H). |
| 77 | | IR (thin film) 2966, 1770, 1736, 1589, 1487, 1193, 1175, 1131, 1008, 730 cm$^{-1}$ | HRMS-ESI (m/z) [M + Na]$^+$ calcd for C$_{24}$H$_{29}$FN$_2$O$_6$SNa, 515.1623; found, 515.1617 | $^1$H NMR (500 MHz, CDCl$_3$) δ 9.84 (d, J = 7.2 Hz, 1H), 8.31 (d, J = 5.4 Hz, 1H), 7.14 (td, J = 8.3, 6.9 Hz, 1H), 6.99 (d, J = 5.4 Hz, 1H), 6.71 (dd, J = 8.3, 2.5 Hz, 1H), 6.64 (dt, J = 11.0, 2.4 Hz, 1H), 6.59 (tdd, J = 8.2, 2.4, 0.9 Hz, 1H), 5.24 (qd, J = 6.5, 4.2 Hz, 1H), 5.11-5.00 (m, 1H), 4.21-4.17 (m, 1H), 3.91 (s, 3H), 2.35 (s, 3H), 2.01-1.93 (m, 1H), 1.37-1.31 (m, 6H), 1.02 (d, J = 4.5 Hz, 3H), 1.00 (d, J = 4.5 Hz, 3H). |
| 78 | | | HRMS-ESI (m/z) [M + H]$^+$ calcd for C$_{27}$H$_{27}$F$_2$N$_2$O$_5$S, 529.1603; found, 529.1600 | $^1$H NMR (400 MHz, CDCl$_3$) δ 9.78 (d, J = 7.3 Hz, 1H), 8.31 (d, J = 5.4 Hz, 1H), 7.32-7.15 (m, 4H), 7.04-6.89 (m, 5H), 5.75 (dq, J = 9.7, 6.1 Hz, 1H), 5.00 (p, J = 7.1 Hz, 1H), 4.06 (d, J = 9.8 Hz, 1H), 3.90 (s, 3H), 2.34 (s, 3H), 1.25 (d, J = 6.2 Hz, 3H), 1.06 (d, J = 7.1 Hz, 3H). <br> $^{19}$F NMR (376 MHz, CDCl$_3$) δ −115.50, −115.85. |

*Cmpd. No.—Compound Number

TABLE 3

Biological Testing Rating Scale
Rating Table for Fungal Pathogens

| % Control | Rating |
|---|---|
| >80 | A |
| ≤80 | B |
| Not Tested | C |
| No Activity Observed in the Reported Assay | D |

TABLE 4

Biological Activity - PUCCRT and SEPTTR Disease Control in High and Low Volume Applications

| | HV activity at 100 ppm | | | | LV activity at 121.5 g/H | | | |
|---|---|---|---|---|---|---|---|---|
| | PUCCRT* | | SEPTTR* | | PUCCRT* | | SEPTTR* | |
| Cmpd. No. | 1DP* | 3DC* | 1DP* | 3DC* | 1DP* | 3DC* | 1DP* | 3DC* |
| 1 | A | A | B | B | C | C | C | C |
| 2 | A | D | A | A | C | C | C | C |
| 3 | A | D | A | A | C | C | C | C |
| 4 | A | D | A | A | C | C | C | C |
| 5 | A | D | A | A | C | C | C | C |
| 6 | A | B | A | A | C | C | C | C |
| 7 | B | D | B | D | C | C | C | C |
| 8 | A | D | B | B | C | C | C | C |
| 9 | A | D | A | A | C | C | C | C |
| 10 | B | D | D | D | C | C | C | C |
| 11 | A | A | A | B | C | C | C | C |
| 12 | A | B | A | B | C | C | C | C |
| 13 | A | B | A | A | C | C | C | C |
| 14 | A | B | A | A | C | C | C | C |
| 15 | D | D | A | D | C | C | C | C |
| 16 | A | A | A | B | C | C | C | C |
| 17 | A | D | B | D | C | C | C | C |
| 18 | A | A | A | A | C | C | C | C |
| 19 | A | A | A | D | C | C | C | C |
| 20 | A | B | A | A | C | C | C | C |
| 21 | D | D | B | B | C | C | C | C |
| 22 | A | B | A | B | C | C | C | C |
| 23 | A | B | A | A | C | C | C | C |
| 24 | A | B | A | A | C | C | C | C |
| 25 | B | D | D | D | C | C | C | C |
| 26 | A | B | A | A | C | C | C | C |
| 27 | B | D | D | B | C | C | C | C |
| 28 | D | D | D | D | C | C | C | C |
| 29 | A | A | A | A | C | C | C | C |
| 30 | A | B | A | A | C | C | C | C |
| 31 | A | B | A | A | C | C | C | C |
| 32 | B | B | B | A | C | C | C | C |
| 33 | A | A | A | B | C | C | C | C |
| 34 | D | D | B | D | C | C | C | C |
| 35 | A | B | A | A | C | C | C | C |
| 36 | A | A | A | B | C | C | C | C |
| 37 | A | A | B | D | C | C | C | C |
| 38 | A | A | A | B | C | C | C | C |
| 39 | B | B | A | A | C | C | C | C |
| 40 | C | C | C | C | D | B | D | D |
| 41 | C | C | C | C | A | A | A | A |
| 42 | C | C | C | C | B | B | B | D |
| 43 | C | C | C | C | A | A | A | B |
| 44 | C | C | C | C | A | B | A | A |
| 45 | C | C | C | C | A | A | A | A |
| 46 | C | C | C | C | A | A | A | A |
| 47 | C | C | C | C | A | B | A | A |
| 48 | C | C | C | C | A | D | A | A |
| 49 | C | C | C | C | B | D | B | D |
| 50 | C | C | C | C | A | A | A | A |
| 51 | C | C | C | C | A | B | A | A |
| 52 | C | C | C | C | A | B | A | A |
| 53 | C | C | C | C | A | B | A | A |
| 54 | C | C | C | C | A | D | A | A |
| 55 | C | C | C | C | D | D | B | D |
| 56 | C | C | C | C | A | A | B | B |
| 57 | C | C | C | C | A | B | A | A |
| 58 | C | C | C | C | A | A | A | A |
| 59 | C | C | C | C | B | B | A | D |
| 60 | C | C | C | C | A | A | B | B |
| 61 | C | C | C | C | A | A | B | A |
| 62 | C | C | C | C | A | A | B | D |
| 63 | C | C | C | C | A | B | A | A |
| 64 | C | C | C | C | A | B | A | A |
| 65 | C | C | C | C | A | A | A | A |
| 66 | C | C | C | C | B | B | D | D |
| 67 | C | C | C | C | A | B | A | A |
| 68 | C | C | C | C | D | B | B | D |
| 69 | C | C | C | C | B | B | D | B |
| 70 | C | C | C | C | A | A | A | A |
| 71 | C | C | C | C | A | A | A | B |
| 72 | C | C | C | C | A | A | A | A |
| 73 | C | C | C | C | A | A | A | A |
| 74 | C | C | C | C | A | B | A | A |
| 75 | C | C | C | C | A | B | A | A |
| 76 | C | C | C | C | D | D | D | D |
| 77 | C | C | C | C | A | A | B | A |
| 78 | C | C | C | C | A | B | A | A |

*Cmpd. No.—Compound Number
*PUCCRT - Wheat Brown Rust (*Puccinia triticina*)
*SEPTTR - Wheat Leaf Blotch (*Zymoseptoria tritici*)
*1DP—1 Day Protectant
*3DC—3 Day Curative
*g/H—Grams Per Hectare
*ppm—Parts Per Million

TABLE 5

Biological Activity - Disease Control at 25 ppm

| | PHAKPA* | |
|---|---|---|
| Cmpd. No. | 1DP* | 3DC* |
| 40 | B | D |
| 61 | A | A |
| 62 | B | B |
| 63 | A | B |
| 64 | A | A |
| 65 | A | B |
| 66 | B | B |
| 67 | A | B |
| 68 | B | D |
| 69 | B | D |
| 70 | A | B |
| 71 | B | D |
| 72 | A | A |
| 73 | A | A |
| 74 | B | B |
| 75 | B | B |
| 76 | B | D |
| 77 | A | B |
| 78 | B | D |

*Cmpd. No.—Compound Number
*PHAKPA—Asian Soybean Rust (*Phakopsora pachyrhizi*)
*1DP—1 Day Protectant
*3DC—3 Day Curative

What is claimed is:
1. A composition for the control of a fungal pathogen including mixtures of at least one of the compounds of Formula I,

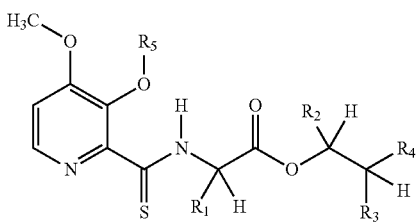

wherein:

$R_1$ is hydrogen or $C_1$-$C_5$ alkyl, substituted with 0,1 or multiple $R_6$;

$R_2$ is hydrogen, $C_1$-$C_5$ alkyl or cycloalkyl, each optionally substituted with 0,1 or multiple $R_6$;

$R_3$ is alkyl, cycloalkyl, alkenyl, aryl or heteroaryl, each optionally substituted with 0,1 or multiple $R_6$;

$R_4$ is alkyl, cycloalkyl, alkenyl, aryl, heteroaryl, alkoxy, aryloxy, heteroaryloxy, each optionally substituted with 0,1 or multiple $R_6$;

$R_5$ is hydrogen, —C(O)$R_7$, or —CH$_2$OC(O)$R_7$;

$R_6$ is hydrogen, alkyl, aryl, acyl, halo, alkenyl, alkynyl, alkoxy, cyano or heterocyclyl, each optionally substituted with 0,1 or multiple $R_8$;

$R_7$ is from alkyl, alkoxy, or aryl, each substituted with 0,1 or multiple $R_6$;

$R_8$ is hydrogen, alkyl, aryl, acyl, halo, alkenyl, alkoxy, or heterocyclyl;

and a phytologically acceptable carrier material.

2. The composition according to claim 1, wherein $R_5$ is hydrogen.

3. The composition according to claim 2, wherein $R_1$ is methyl, $R_2$ is $C_1$-$C_5$ alkyl, $R_3$ and $R_4$ independently are aryl, each optionally substituted with 0, 1, or multiple $R_6$.

4. The composition according to claim 1, wherein $R_5$ is chosen from —C(O)$R_7$, or —CH$_2$OC(O)$R_7$.

5. The composition according to claim 4, wherein $R_7$ is alkyl, optionally substituted with 0, 1, of multiple $R_6$.

6. The composition according to claim 5, wherein $R_1$ is methyl, $R_2$ is $C_1$-$C_5$ alkyl, $R_3$ and $R_4$ independently are aryl, each optionally substituted with 0, 1, or multiple $R_6$.

7. The compound according to claim 6, wherein $R_7$ is chosen from —CH$_3$, —CH$_2$OCH$_2$CH$_3$, —CH$_2$CH$_2$OCH$_3$, —CH(CH$_3$)$_2$, —CH$_2$CH$_2$CH$_2$CH$_3$, or -cyclopropyl.

* * * * *